US011723886B2

(12) United States Patent
Kelley et al.

(10) Patent No.: US 11,723,886 B2
(45) Date of Patent: *Aug. 15, 2023

(54) TARGETING OCULAR DISEASES WITH NOVEL APE1/REF-1 INHIBITORS

(71) Applicant: Indiana University Research and Technology Corporation, Indianapolis, IN (US)

(72) Inventors: Mark R. Kelley, Zionsville, IN (US); Timothy W. Corson, Fishers, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 99 days.

This patent is subject to a terminal disclaimer.

(21) Appl. No.: 16/968,009

(22) PCT Filed: Feb. 7, 2019

(86) PCT No.: PCT/US2019/017023
§ 371 (c)(1),
(2) Date: Aug. 6, 2020

(87) PCT Pub. No.: WO2019/157163
PCT Pub. Date: Aug. 15, 2019

(65) Prior Publication Data
US 2021/0393556 A1 Dec. 23, 2021

Related U.S. Application Data

(60) Provisional application No. 62/628,093, filed on Feb. 8, 2018.

(51) Int. Cl.
*A61K 31/165* (2006.01)
*A61P 27/02* (2006.01)
(Continued)

(52) U.S. Cl.
CPC .......... *A61K 31/165* (2013.01); *A61K 31/445* (2013.01); *A61K 31/45* (2013.01);
(Continued)

(58) Field of Classification Search
CPC .... A61K 31/165; A61K 31/445; A61K 31/45; A61K 31/675; A61K 45/06; A61K 31/20;
(Continued)

(56) References Cited

U.S. PATENT DOCUMENTS 5,210,239 A 5/1993 Abe et al.
2016/0045461 A1 2/2016 Kelley et al.

FOREIGN PATENT DOCUMENTS

WO 2009042542 A1 4/2009
WO 2012167122 A1 12/2012
WO WO-2012167122 A1 * 12/2012 ............. A61K 31/12

OTHER PUBLICATIONS

Aihua Jiang, Hua Gao, Mark R. Kelley, Xiaoxi Qiao, Inhibition of APE1/Ref-1 redox activity with APX3330 blocks retinal angiogenesis in vitro and in vivo, Vision Research 51 (2011) 93-100 (Year: 2011).*

(Continued)

*Primary Examiner* — San Ming R Hui
(74) *Attorney, Agent, or Firm* — Stinson LLP

(57) ABSTRACT

[[(2E)-2-[(3-methoxy-1,4-dioxo-1,4-dihydronaphthalen-2-yl)methylidene]-N,N-diethylpentanamide] (APX2009) and (2E)-2-[(3-methoxy-1,4-dioxo-1,4-dihydronapthalen-2-yl)methylidene]-N-methoxypentanamide] (APX2014) for inhibiting ocular diseases are disclosed herein.

9 Claims, 28 Drawing Sheets

(51) Int. Cl.
- A61K 31/445 (2006.01)
- A61K 31/45 (2006.01)
- A61K 31/675 (2006.01)
- A61K 45/06 (2006.01)

(52) U.S. Cl.
CPC ............ *A61K 31/675* (2013.01); *A61K 45/06* (2013.01); *A61P 27/02* (2018.01)

(58) Field of Classification Search
CPC ........ A61K 31/122; A61P 27/02; A61P 35/00; C07C 50/06; C07C 50/12
See application file for complete search history.

(56) References Cited

OTHER PUBLICATIONS

Basavarajappa et al., Synthesis and Mechanistic Studies of a Novel Homoisoflavanone Inhibitor of Endothelial Cell Growth; PLOS one; 2014, vol. 9, No. 4, 11-pages.

Basavarajappa et al., Ferrochelatase is a therapeutic target for ocular neovascularization; EMBO Molecular Medicine; 2017, vol. 9, No. 6, 16-pages.

Biswas et al., Endothelial cell tumor growth is APE/ref-1 dependent; Am J. Physiol Cell Physiol 309, 2015, pp. C296-C307.

Cardoso et al., APE1/Ref-1 Regulates STAT3 Transcriptional Activity and APE1/Ref-1-STAT3 Dual-Targeting Effectively Inhibits Pancreatic Cancer Cell Survival; PLOS one; 2012, vol. 7, No. 10, 13-pages.

Chiarini et al., Tissue Biology of Apoptosis: Ref-1 and Cell Differentiation in the Developing Retina; Annals of the New York Academy of Sciences; 2000, vol. 926, pp. 64-78.

Compochiaro et al., Ocular Neovascularization; J Mol Med (Berl); 2013, vol. 91, No. 3, pp. 311-321.

Evans et al., The *Saccharomyces cerevisiae* Msh2 Mismatch Repair Protein Localizes to Recombination Intermediates In Vivo; Molecular Cell, 2000, vol. 5, pp. 789-799.

Falavarjani et al., Adverse events and complications associated with intravitreal injection of anti-VEGF agents: a review of literature; Eye, 2013, vol. 27, pp. 787-794.

Fishel et al., Inhibition of the Redox Function of Ape1/Ref-1 in Myeloid Leukemia Cell Lines Results in a Hypersensitive Response to Retinoic Acid-induced Differentiation and Apoptosis; Exp Hematol., 2010, vol. 38, No. 12, pp. 1178-1188.

Fishel et al., Impact of APE1/Ref-1 Redox Inhibition on Pancreatic Tumor Growth; Molecular Cancer Therapeutics; 2011, vol. 10, No. 9, 12-pages.

Fishel et al., Apurinic/Apyrimidinic Endonuclease/Redox Factor-1 (APE1/Ref-1) Redox Function Negatively Regulates NRF2*; The Journal of Biological Chemistry; 2015, vol. 290, No. 5, pp. 3057-3068.

Grossniklaus et al., Animal Models of Choroidal and Retinal Neovascularization; Prog Retin Eye Res., 2010, vol. 29, No. 6, pp. 500-519.

Jiang et al., Inhibition of APE1/Ref-1 Redox Activity with APX3330 Blocks Retinal Angiogenesis in vitro and in vivo; Vison Res., 2011, vol. 51, No. 1, pp. 93-100.

Kelley et al., Functional Analysis of Novel Analogues of E3330 That Block the Redox Signaling Activity of the Multi-functional AP Endonuclease/Redox Signaling Enzyme APE1/Ref-1; Antioxidants & Redox Signaling; 2011, vol. 14, No. 1, 16-pages.

Lando et al., A Redox Mechanism Controls Differential DNA Binding Activities of Hypoxia-inducible Factor (HIF) 1a and the HIF-like Factor*; The Journal of Biological Chemistry; 2000, vol. 275, No. 7, pp. 4618-4627.

Li et al, Structure of a bacterial homolog of vitamin K epoxide reductase; Nature, 2010, vol. 463, No. 7280, pp. 507-512.

Li et al., Inhibition of APE1/Ref-1 redox activity rescues human retinal pigment epithelial cells from oxidative stress and reduces choroidal neovascularization; Redox Biology 2, 2014, pp. 485-494.

Li et al., Determinants beyond Both Complementarity and Cleavage Govern MicroR159 Efficacy in *Arabidopsis*; PLOS/Genetics; 2014, vol. 10, No. 3, 20-pages.

Logsdon et al., Regulation of HIF1a under Hypoxia by APE1/Ref-1 Impacts CA9 Expression: Dual Targeting in Patient-Derived 3D Pancreatic Cancer Models; Cancer Biology and Signal Transduction; 2016, 12-pages.

Lou et al., Role of the Multifunctional DNA Repairand Redox Signaling Protein Ape1/Ref-1 in Cancer and Endothelial Cells: Small-Molecule Inhibition of the Redox Function of Ape1; Antioxidants & Redox Signaling; 2008, vol. 10, No. 11, 16-pages.

Lou et al., Characterization of the redox activity and disulfide bond formation in Apurinic/apyrimidinic endonuclease; Biochemistry, 2012; vol. 51, No. 2, pp. 695-705.

Lou et al., Aberrant expression of redox protein Ape1 in colon cancer stem cells; Oncology Letters; 2014, vol. 7, pp. 1078-1082.

Lux et al., Non-responders to bevacizumab (Avastin) therapy of choroidal neovascular lesions; Br J Ophthalmol, 2007, vol. 91, pp. 1318-1322.

McIlwain et al., APE1/Ref-1 redox-specific inhibition decreases survivin protein levels and induces cell cycle arrest in prostate cancer cells; Oncotarget, 2018, vol. 9, No. 13, pp. 10962-10977.

Nishi et al., Vascular Endothelial Growth Factor Receptor-1 Regulates Postnatal Angiogenesis Through Inhibition of the Excessive Activation of Akt; Circulation Research; 2008, 8-pages.

Poor et al., Reliability of the Mouse Model of Choroidal Neovascularization Induced by Laser Photocoagulation; Retina; The Association for Research in Vision and Ophthalmogy, Inc., 2014, vol. 55, No. 10, 10-pages.

Prasad et al., Age-related macular degeneration: Current and novel therapies; Maturitas; 2010, pp. 46-50.

Seo et al., Selenomethionine regulation of p53 by a ref1-dependent redox mechanism; PNAS, 2002, vol. 99, No. 22, 6-pages.

Shah et al., Exploiting the Ref-1-APE1 node in cancer signaling and other diseases: from bench to clinic; NPJ/Precision Oncology; 2017; 19-pages.

Su et al., Interactions of APE1 with a redox inhibitor: Evidence for an alternate conformation of the enzyme; Biochemistry; 2011, vol. 50, No. 1, pp. 82-92.

Sulaiman et al., A Simple Optical Coherence Tomography Quantification Method for Choroidal Neovascularization; Journal of Ocular Pharmacology and Therapeutics; 2015, vol. 31, No. 8, 8-pages.

Sulaiman et al., A novel small moleucle ameliorates ocular neovascularisation and synergises with anti-VEGF therapy; Nature, Scientific Reports; 2015, 11-pages.

Wenzel et al., Optical coherence tomography enables imaging of tumor initiation in the TAg-RB mouse model of retinoblastoma; Molecular Vision, 2015, vol. 21, pp. 515-522.

Xanthoudakis et al., Identification and characterization of Ref-1, a nuclear protein that facilitates AP-1 DNA-binding activity; The EMBO Journal, 1992, vol. 11, No. 2, pp. 663-655.

Xanthoudakis et al., Redox activation of Fos-Jun DNA binding activity is mediated by a DNA repair enzyme; The EMBO Journal, 1992, vol. 11, No. 9, pp. 3323-3335.

Zhang et al., Inhibition of Apurinic/apyrimidinic endonuclease I's redox activity revisited; Biochemistry, 2013, vol. 52, No. 17, pp. 2955-2966.

Fishel et al., Inhibitioin of Redox Function of APE1/Ref-1 in Myeloid Leukemia Cell Lines Results in a Hypersensitive Response to Retinoic Acidf-induced Differentation and Apoptosis; Exp Hematol., Dec. 2010; vol. 31, No. 12, pp. 1178-1188.

* cited by examiner

TARGETING OCULAR DISEASES WITH NOVEL APE1/REF-1 INHIBITORS

CROSS-REFERENCE TO RELATED APPLICATION

The present disclosure claims priority to International Patent Application Serial No. PCT/US2019/017023 (published as WO 2019/157163), which was filed Feb. 7, 2019, and which claims priority to U.S. Provisional Application No. 62/628,093, filed Feb. 8, 2018, the disclosures of which are hereby incorporated by reference in their entireties.

BACKGROUND OF THE DISCLOSURE

The present disclosure relates generally to the use of 3-[(5-(2,3-dimethoxy-6-methyl1,4-benzoquinoyl)]-2-nonyl-2-proprionic acid (APX3330) and/or its derivatives (e.g., [(2E)-2-[(3-methoxy-1,4-dioxo-1,4-dihydro naphthalen-2-yl)methylidene]-N,N-diethylpentanamide] (APX2009), and (2E)-2-[(3-methoxy-1,4-dioxo-1,4-dihydronapthalen-2-yl)methylidene]-N-methoxypentanamide] (APX2014)) for inhibiting ocular diseases.

Ocular neovascularization is the key pathobiological feature of diseases like proliferative diabetic retinopathy (PDR), retinopathy of prematurity (ROP), and wet age-related macular degeneration (AMD), which together are major causes of blindness (Campochiaro, 2013). In PDR and ROP, abnormal blood vessels grow in and on the retina, while in wet AMD, neovessels grow from the pigmented, subretinal choroid layer into the retina. In all cases, neovessels disrupt retinal architecture and can hemorrhage, leading to blindness. Although the exact stimuli promoting neovascularization are not always well characterized, hypoxia and inflammation both play crucial roles. The currently used, FDA approved pharmacological treatments for these diseases are all biologics targeting the vascular endothelial growth factor (VEGF) signaling pathway, such as ranibizumab and aflibercept (Prasad et al., 2010). Although these therapeutic agents have been very successful, significant proportions of patients are resistant and refractory (Lux et al., 2007; Falavarjani and Nguyen, 2013). Moreover, serious side effects including hemorrhage and endophthalmitis are possible. Therefore, development of novel therapeutic approaches targeting other signaling pathways is crucial.

Inflammation and hypoxia pay crucial role in neovascularization. Treatments that impinge upon both proinflammatory and hypoxic signaling offer a unique therapeutic strategy. One such potential target is the reduction-oxidation factor 1-apurinic/apyrimidinic endonuclease (Ref-1/APE1), an intracellular signaling nexus with important roles in transducing proangiogenic stimuli. This bifunctional protein has an endonuclease role essential for base excision repair (APE1), while the Ref-1 activity is a redox-sensitive transcriptional activator (Shah et al., 2017). Ref-1 redox signaling is a highly regulated process that reduces oxidized cysteine residues in specific transcription factors as part of their transactivation (Xanthoudakis and Curran, 1992; Xanthoudakis et al., 1992; Evans et al., 2000; Lando et al., 2000; Nishi et al., 2002; Seo et al., 2002; Li et al., 2010; Fishel et al., 2011; Cardoso et al., 2012; Kelley et al., 2012; Luo et al., 2012; Zhang et al., 2013; Fishel et al., 2015; Logsdon et al., 2016). This redox signaling affects numerous transcription factors including HIF-1α, NF-κB, and others. The regulation of HIF-1α and NF-κB are particularly relevant to angiogenesis and eye diseases (Evans et al., 2000; Nishi et al., 2002; Seo et al., 2002; Fishel et al., 2011; Cardoso et al., 2012; Fishel et al., 2015; Logsdon et al., 2016).

Excitingly, Ref-1 activity can be targeted pharmacologically. 3-[(5-(2,3-dimethoxy-6-methyl1,4-benzoquinoyl)]-2-nonyl-2-proprionic acid, (APX3330; formerly called E3330) is a specific Ref-1/APE1 redox inhibitor. APX3330 has been extensively characterized as a direct, highly selective inhibitor of Ref-1 redox activity that does not affect the protein's endonuclease activity (Luo et al., 2008; Fishel et al., 2010; Su et al., 2011; Cardoso et al., 2012; Luo et al., 2012; Zhang et al., 2013; Fishel et al., 2015). Ref-1/APE1 is highly expressed during retinal development, and in retinal pigment epithelium (RPE) cells, pericytes, choroidal endothelial cells and retinal endothelial cells (Chiarini et al., 2000; Jiang et al., 2011; Li et al., 2014a), and more generally, Ref-1 is frequently upregulated in regions of tissues in which inflammation is present (Zou et al., 2009; Kelley et al., 2010). APX3330 was previously shown to block in vitro angiogenesis, as evidenced by proliferation, migration, and tube formation of retinal and choroidal endothelial cells (Jiang et al., 2011; Li et al., 2014b). Indeed, APX3330 delivered intravitreally (directly into the eye) reduced neovascularization in the very low density lipoprotein receptor (VLDLR) knockout mouse model of retinal neovascularization (Jiang et al., 2011), and also in laser-induced choroidal neovascularization (L-CNV) (Li et al., 2014b), the most widely used animal model that recapitulates features of wet AMD (Grossniklaus et al., 2010).

While the lead clinical candidate is efficacious in preclinical cancer studies, a second generation Ref-1 inhibitors that would have increased efficacy in antiangiogenic and anti-inflammatory transcription factor (NF-κB, HIF-1α) inhibition, as well as new chemical properties, is desired.

BRIEF DESCRIPTION

The present disclosure is directed to the use of 3-[(5-(2,3-dimethoxy-6-methyl1,4-benzoquinoyl)]-2-nonyl-2-proprionic acid (APX3330) and/or its derivatives, such [(2E)-2-[(3-methoxy-1,4-dioxo-1,4-dihydronaphthalen-2-yl)methylidene]-N,N-diethylpentanamide] (APX2009) and (2E)-2-[(3-methoxy-1,4-dioxo-1,4-dihydronapthalen-2-yl)methylidene]-N-methoxypentanamide] (APX2014), for inhibiting ocular neovascularization. Particularly, it was found that APX2009 and APX2014 provided enhanced inhibition of Ref-1 function in a DNA-binding assay compared to APX3330. Both compounds were antiproliferative against human retinal microvascular endothelial cells (HRECs; GI50 APX2009: 1.1 µM, APX2014: 110 nM) and macaque choroidal endothelial cells (Rf/6a GI50 APX2009: 26 µM, APX2014: 5.0 µM). Both compounds significantly reduced the ability of HRECs and Rf/6a cells to form tubes at mid nanomolar concentrations compared to control, and both significantly inhibited HREC and Rf/6a cell migration in a scratch wound assay.

Ex vivo, both APX2009 and APX2014 inhibited choroidal sprouting at low micromolar and high nanomolar concentrations respectively. In the laser-induced choroidal neovascularization mouse model, intraperitoneal APX2009 treatment significantly decreased lesion volume by 4-fold compared to vehicle (p<0.0001, ANOVA with Dunnett's post hoc tests), without obvious intraocular or systemic toxicity. Thus, Ref-1 inhibition with APX2009 and APX2014 blocks ocular angiogenesis in vitro and ex vivo, and APX2009 is an effective systemic therapy for CNV in vivo, establishing Ref-1 inhibition as a promising therapeutic approach for ocular neovascularization.

Accordingly, in one aspect, the present disclosure is directed to a method of inhibiting ocular neovascularization in a subject in need thereof. The method includes administering to the subject an effective amount of an apurinic/apyrimidinic endonuclease 1 redox factor 1 (APE1/Ref-1) inhibitor, pharmaceutically acceptable salts or pharmaceutically acceptable solvates thereof.

In another aspect, the present disclosure is directed to a method of inhibiting ocular neovascularization in a subject in need thereof, the method comprising administering to the subject an effective amount of an apurinic/apyrimidinic endonuclease 1 redox factor 1 (APE1/Ref-1) inhibitor, pharmaceutically acceptable salts or pharmaceutically acceptable solvates thereof.

In another aspect, the present disclosure is directed to a method of treating retinopathy of prematurity (ROP) in a subject in need thereof, the method comprising administering to the subject an effective amount of an apurinic/apyrimidinic endonuclease 1 redox factor 1 (APE1/Ref-1) inhibitor, pharmaceutically acceptable salts or pharmaceutically acceptable solvates thereof.

In yet another aspect, the present disclosure is directed to a method of treating wet age-related macular degeneration (AMD) in a subject in need thereof, the method comprising administering to the subject an effective amount of an apurinic/apyrimidinic endonuclease 1 redox factor 1 (APE1/Ref-1) inhibitor, pharmaceutically acceptable salts or pharmaceutically acceptable solvates thereof.

DESCRIPTION OF THE FIGURES

The disclosure will be better understood, and features, aspects and advantages other than those set forth above will become apparent when consideration is given to the following detailed description thereof. Such detailed description makes reference to the following drawings, wherein:

FIG. 1A depicts the synthetic scheme for APX2009 (6a) and APX2014 (6b). Structure of APX3330 (7) included for reference. Reagents and conditions: a, 2-iodo-3-hydroxy-1,4-naphthoquinone (iodolawsone, 1), 2-propylacrylic acid (2), $K_2CO_3$, $Pd(OAc)_2$, argon, 100° C., 1 hour, 74%; b, $(COCl)_2$, DMF, DCM, RT overnight, 100%; c, $DEA \cdot HCl$ (APX2009) or $CH_3ONH_2 \cdot HCl$ (APX2014), HCl, RT, 45 minute, 62% and 71% respectively; d, $NaOCH_3/CH_3OH$, argon, 30 minutes, RT, 96% and 86%, respectively. FIG. 1B shows that APX2009 and APX2014 are more effective inhibitors of Ref-1-induced AP-1 DNA binding than APX3330 in an EMSA. Two separate gels from the same experiment are shown. The IC50 for redox EMSA inhibition was 25, 0.45 and 0.2 μM for APX3330, APX2009 and APX2014, respectively. These assays were performed multiple times with similar results.

FIG. 3B shows quantification of EdU and FIG. 3D shows quantification of Ki-67 in HRECs. Mean±S.E.M., n=3 fields per dose. \*\*, p<0.01; \*\*\*\*, p<0.0001 compared to DMSO control (one-way ANOVA with Dunnett's post hoc test). Representative data from three independent experiments. See FIGS. 4A & 5.

FIG. 6A shows TUNEL staining (red) for cell death and DAPI (blue) for nuclear staining. No TUNEL-positive cells are observed in these images. Staurosporine acts as a positive control. Scale bar=100 μm. FIG. 6B shows quantification data showing the percentage of TUNEL positive cells upon various treatments. Mean±S.E.M., n=3. ns, non-significant (One-way ANOVA with Dunnett's post hoc tests). Representative data from two independent experiments.

FIG. 7A depicts the effect of APX2009 and APX2014 on cell migration in HRECs. A confluent monolayer of HRECs with various treatments (highest doses shown) was wounded and wound closure was monitored for 8 hours. FIG. 7B shows quantitative analysis of cell migration, showing that APX compounds significantly block the migration of HRECs. FIG. 7C depicts the effects of APX2009 and APX2014 on cell migration in Rf/6a cells. A confluent monolayer of Rf/6a with various treatments (highest doses shown) was wounded and wound closure was monitored for 16 hours. FIG. 7D shows quantitative analysis of cell migration, showing that APX compounds significantly block the migration of Rf/6a cells. Mean±S.E.M., n=3 per dose. \*\*, p<0.01; \*\*\*, p<0.001 compared to DMSO control (one-way ANOVA with Dunnett's post hoc test). Scale bar=500 μm.

FIG. 9A depicts tube formation on Matrigel by HRECs in the presence of the indicated concentrations of APX compounds; FIG. 9B shows a quantitative analysis of APX2009 and APX2014 compounds on HREC tube formation. Tubular length was measured and represented as relative to DMSO control. FIG. 9C depicts tube formation on Matrigel by Rf/6a in the presence of the indicated concentrations of APX compounds; FIG. 9D shows a quantitative analysis of APX2009 and APX2014 compounds on Rf/6a tube formation. Tubular length was measured and represented as relative to DMSO control. Mean±S.E.M., n=3 wells. , p<0.01; *, p<0.001 compared to DMSO control (one-way ANOVA with Dunnett's post hoc test). Representative data from three independent experiments. Scale bar=500 µm.

(FIG. 11B) VEGFA, (FIG. 11C) VCAM1, and (FIG. 11D) CCL20 mRNA expression levels in HRECs. APX2009 and APX2014 dose dependently inhibited levels of each transcript. Mean±S.E.M., n=3 technical replicates. *, p<0.05; , p<0.01; *, p<0.001 compared to DMSO control (one-way ANOVA with Dunnett's post hoc test). Representative data from three independent experiments.

FIG. 12A is representative phase contrast images of choroidal sprouts formed 48 hours after treatment with indicated APX2009 concentrations or vehicle (0.5% DMSO) control. FIG. 12B shows quantification of sprouting distance from the edge of the APX2009-treated choroidal tissue piece to the end of the sprouts averaged from four perpendicular directions using ImageJ software. FIG. 12C is representative images of choroidal sprouts formed 48 hours after treatment with indicated APX2014 concentrations or vehicle (0.2% DMSO) control. FIG. 12D shows quantification of sprouting distance from the edge of the choroidal tissue piece to the end of the sprouts averaged from four perpendicular directions using ImageJ software. Mean±S.E.M., n=4-5 choroids/per treatment; N=3-4 eyes.*, p<0.001; **, p<0.0001 (ANOVA with Dunnett's post hoc test). Scale bars=500 µm.

FIG. 13A shows representative optical coherence tomography (OCT) images obtained 7 days post-laser, showing CNV lesions in eyes of vehicle (left) and 50 mg/kg i.p. APX3330 (right) treated animals. FIG. 13B shows representative images from confocal microscopy for agglutinin-stained CNV lesions 14 days post-laser treatment. FIG. 13C shows quantification of CNV lesion vascular volumes from Z-stack images at day 14 using ImageJ software. Mean±S.E.M., n=7-9 eyes/treatment. * p<0.05 (unpaired Student's t-test). Scale bars=100 µm.

FIG. 14A shows representative OCT images obtained 7 and 14 days post-laser, showing CNV lesions of untouched control, vehicle, 12.5 mg/kg and 25 mg/kg APX2009 compound i.p. injected twice daily until 14 days post-laser treatment. FIG. 14B depicts fluorescein angiography (FA) of CNV showing the vascular leakage suppression by APX2009. FIG. 14C is representative images from confocal microscopy for agglutinin-stained CNV lesions 14 days post-laser treatment. FIG. 14D shows quantification of CNV lesion vascular volumes from Z-stack images at day 14 using ImageJ software. Mean±S.E.M., n=8-10 eyes/treatment. ns, non-significant; ***, p<0.001 compared to DMSO control (one-way ANOVA with Tukey's post hoc test). Scale bars=100 µm.

FIG. 15A depicts Double-stained Agglutinin and *Griffonia simplicifolia* isolectin B4 (GSIB4) confocal images in the L-CNV lesions 14 days post-laser treatment. FIG. 15B shows quantification of CNV lesion vascular volumes from Z-stack of GS-IB4-stained images at day 14 using ImageJ software. ns, non-significant; ****, p<0.0001 (One-way ANOVA with Tukey's post hoc tests). FIG. 15C shows quantification of mouse body weight of vehicle and APX2009 injected groups over 14 days. No significant difference in weight between treatments was observed at any time point (repeated measures two-way ANOVA). Mean±S.E.M., n=8-10 eyes/treatment. Scale bars=100 µm.

DETAILED DESCRIPTION

Figure 1A:
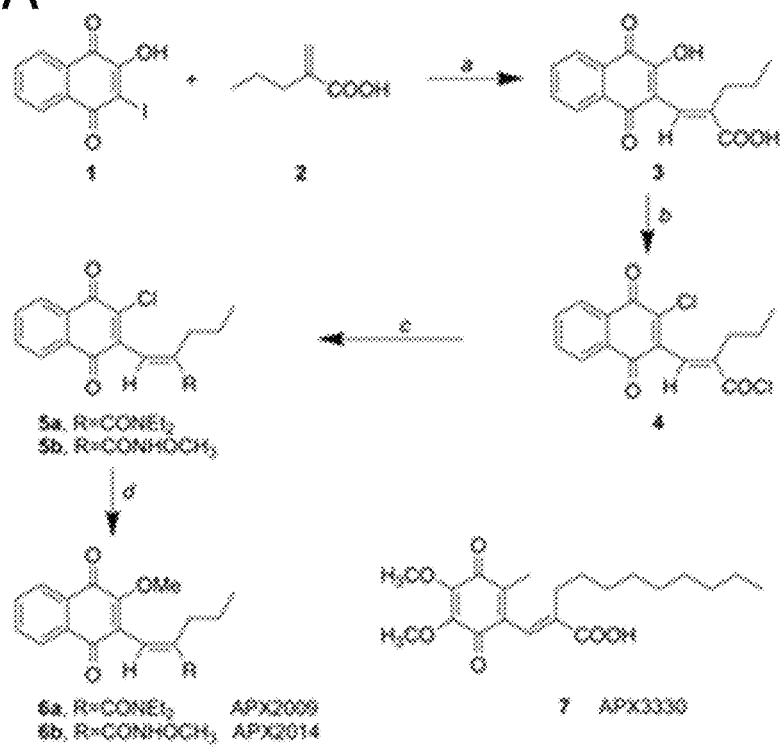
FIGS. 1A & 1B depict the synthesis and activity of Ref-1 inhibitors.

The present disclosure relates generally to APE1 inhibitors, such as 3-[(5-(2,3-dimethoxy-6-methyl1,4-benzoquinoyl)]-2-nonyl-2-proprionic acid (APX3330) and/or its derivatives (e.g., [(2E)-2-[(3-methoxy-1,4-dioxo-1,4-dihydronaphthalen-2-yl)methylidene]-N,N-diethylpentanamide] (APX2009) and (2E)-2-[(3-methoxy-1,4-dioxo-1,4-dihydronapthalen-2-yl)methylidene]-N-methoxypentanamide] (APX2014)) for inhibiting ocular neovascularization. Moreover, the present disclosure is directed to the use of APX2009 and APX2014 for treating diseases like proliferative diabetic retinopathy (PDR), retinopathy of prematurity (ROP), and wet age-related macular degeneration (AMD).

In suitable embodiments, the present disclosure includes administering to a subject in need thereof an effective amount of an APE1 inhibitor, the APE1 inhibitor capable of interacting with the APE1 protein such to cause unfolding of the APE1 protein in the amino terminal portion of APE1, inhibiting the ability of APE1 to interact with other proteins in the neurons or to perform its redox signaling function. More particularly, APE1 inhibitors used in the present disclosure block the ability of APE1/Ref-1 to convert NF-κB and AP-1 from an oxidised state to reduced state, thereby altering their transcriptional activity.

Accordingly, in particular suitable embodiments, the APE1 inhibitor has the formula:

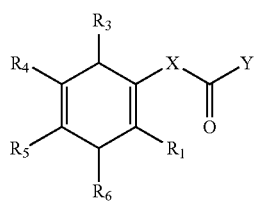

Formula (I)

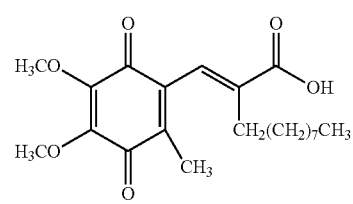
APX3330 wherein $R_1$ is selected from the group consisting of alkyl, alkoxy, hydroxyl, and hydrogen; $R_2$ is an alkyl; $R_3$ and $R_6$ are independently selected from the group consisting of an alkoxy and aryl; $R_4$ and $R_5$ are independently selected from the group consisting of an alkoxy and aryl, or both $R_4$ and $R_5$ taken together form a substituted or unsubstituted napthoquinone;

X is selected from the group consisting of CH=CR$_2$ and NCH, wherein R$_2$ is selected from the group consisting of $C_1$-$C_{10}$ alkyl and $CF_3CH_2CH_2$; and Y is selected from the group consisting of N(Rz)R$_2$ or NR^OR^, wherein each Rz is independently selected from the group consisting of $C_1$-$C_6$ alkyl, heteroalkyl, cycloalkyl and cycloheteroalkyl, straight or branched chain or optionally substituted, or both Rz and R2 taken together with the attached nitrogen form an optionally substituted heterocycle; where each R^ is independently selected from the group consisting of hydrogen, alkyl, heteroalkyl, cyclohexyl, and cycloheteroalkyl, each of which is optionally substituted, or both R^ are taken together with the attached nitrogen and oxygen to form an optionally substituted heterocycle.

Particularly suitable APE1 inhibitors include 3-[(5-(2,3-dimethoxy-6-methyl1,4-benzoquinoyl)]-2-nonyl-2-propionic acid, (hereinafter "E3330" or "3330" or "APX3330"), and/or its analogs (e.g., [(2E)-2-[(3-methoxy-1,4-dioxo-1,4-dihydronaphthalen-2-yl)methylidene]-N,N-diethylpentanamide] (hereinafter "APX2009"), (2E)-2-[(3-methoxy-1,4-dioxo-1,4-dihydronapthalen-2-yl)methylidene]-N,N-dimethylpentanamide] (hereinafter "APX2007"), (2E)-2-[(3-methoxy-1,4-dioxo-1,4-dihydronapthalen-2-yl)methylidene]-N-methoxypentanamide] (hereinafter "APX2014"), (2E)-2-(3-methoxy-1,4-dioxo-1,4-dihydronaphthalen-2-yl)-N,N,2-trimethylprop-2-enamide (hereinafter "APX2032")). Additional suitable analogs are shown below and in Table 1. Further information on APX3330 may be found in Abe et al., U.S. Pat. No. 5,210,239, and information on APX2009 may be found in Kelley et al., J Pharmacol Exp Ther. 2016 November, 359(2): 300-309, each incorporated herein by reference to the extent they are consistent herewith.

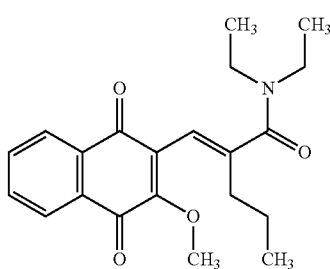
APX2009

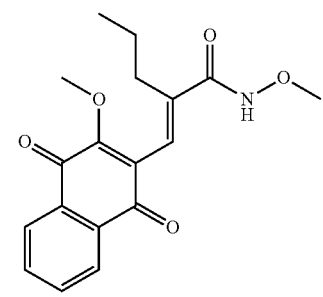
APX2014

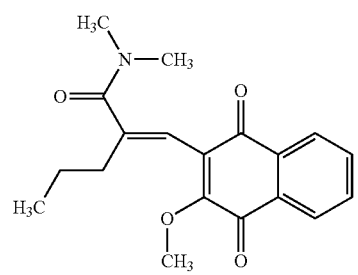
APX2007

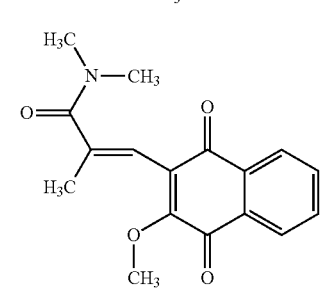
APX2032

TABLE 1

| COMPOUND ID | $R_1$ | X | C(=O)Y | $R_2$ | $R_3$ | $R_4$ | $R_5$ | $R_6$ | EF | MW |
|---|---|---|---|---|---|---|---|---|---|---|
| APX3330 | $CH_3$ | CH=CR$_2$ | OH | $C_9H_{19}$ | =O | MeO | MeO | =O | $C_{21}H_{30}O_6$ | 378.459 |
| APX2006 | MeO | CH=CR$_2$ | NMe | $C_3H_7$ | =O | napthoquinone | | =O | $C_{18}H_{19}NO_4$ | 313.353 |
| APX2007 | MeO | CH=CR$_2$ | N(Me)$_2$ | $C_3H_7$ | =O | napthoquinone | | =O | $C_{19}H_{21}NO_4$ | 327.38 |
| APX2008 | MeO | CH=CR$_2$ | NEt | $C_3H_7$ | =O | napthoquinone | | =O | $C_{19}H_{21}NO_4$ | 327.38 |
| APX2009 | MeO | CH=CR$_2$ | N(Et)$_2$ | $C_3H_7$ | =O | napthoquinone | | =O | $C_{21}H_{25}NO_4$ | 355.428 |
| APX2010 | CH3 | CH=CR$_2$ | NCH$_3$ | $C_4H_9$ | =O | napthoquinone | | =O | $C_{17}H_{23}NO_5$ | 321.373 |
| APX2011 | CH3 | CH=CR$_2$ | N(CH$_3$)$_2$ | $C_4H_9$ | =O | napthoquinone | | =O | $C_{20}H_{23}NO_3$ | 325.408 |
| APX2012 | $CH_3$ | CH=CR$_2$ | NCH$_2$CH$_3$ | $C_4H_9$ | =O | napthoquinone | | =O | $C_{20}H_{23}NO_3$ | 325.408 |

TABLE 1-continued

| COMPOUND ID | $R_1$ | X | C(=O)Y | $R_2$ | $R_3$ | $R_4$ | $R_5$ | $R_6$ | EF | MW |
|---|---|---|---|---|---|---|---|---|---|---|
| APX2013 | $CH_3$ | $CH=CR_2$ | $N(Et)_2$ | $C_4H_9$ | =O | napthoquinone | | =O | $C_{22}H_{27}NO_3$ | 353.462 |
| APX2014 | MeO | $CH=CR_2$ | NOMe | $C_3H_7$ | =O | napthoquinone | | =O | $C_{18}H_{19}NO_5$ | 329.352 |
| APX2015 | $CH_3$ | $CH=CR_2$ | N-cPro | $C_4H_9$ | =O | napthoquinone | | =O | $C_{21}H_{23}NO_3$ | 337.419 |
| APX2016 | $CH_3$ | $CH=CR_2$ | NOMe | $C_4H_9$ | =O | napthoquinone | | =O | $C_{19}H_{21}NO_4$ | 327.38 |
| APX2017 | $CH_3$ | $CH=CR_2$ | N—Et-Pip | $C_4H_9$ | =O | napthoquinone | | =O | $C_{24}H_{30}N_2O_3$ | 394.515 |
| APX2018 | $CH_3$ | $CH=CR_2$ | N-cHexyl | $C_4H_9$ | =O | napthoquinone | | =O | $C_{24}H_{29}NO_3$ | 379.492 |
| APX2019 | $CH_3$ | $CH=CR_2$ | 2-Piperdone | $C_4H_9$ | =O | napthoquinone | | =O | $C_{22}H_{24}N_2O_4$ | 380.444 |
| APX2020 | $CH_3$ | $CH=CR_2$ | N(Me)OMe | $C_4H_9$ | =O | napthoquinone | | =O | $C_{20}H_{23}NO_4$ | 341.407 |
| APX2021 | $CH_3$ | $CH=CR_2$ | E-Morpholino | $C_4H_9$ | =O | napthoquinone | | =O | $C_{22}H_{25}NO_4$ | 367.445 |
| APX2022 | $CH_3$ | $CH=CR_2$ | Z-Morpholino | $C_4H_9$ | =O | napthoquinone | | =O | $C_{22}H_{25}NO_4$ | 367.445 |
| APX2023 | $CH_3$ | $CH=CR_2$ | $NH_2$ | $C_4H_9$ | =O | napthoquinone | | =O | $C_{18}H_{19}NO_3$ | 297.348 |
| APX2024 | $CH_3$ | $CH=CR_2$ | $E-NCH_2CH_2OMe$ | $C_4H_9$ | =O | napthoquinone | | =O | $C_{21}H_{25}NO_4$ | 355.434 |
| APX2025 | $CH_3$ | $CH=CR_2$ | $Z-NCH_2CH_2OMe$ | $C_4H_9$ | =O | napthoquinone | | =O | $C_{21}H_{25}NO_4$ | 355.434 |
| APX2026 | Cl | $CH=CR_2$ | NOMe | $C_3H_7$ | =O | napthoquinone | | =O | $C_{17}H_{16}ClNO_4$ | 333.77 |
| APX2027 | Cl | $CH=CR_2$ | $N(Et)_2$ | $C_3H_7$ | =O | napthoquinone | | =O | $C_{20}H_{22}ClNO_3$ | 359.85 |
| APX2028 | OH | CH=CR2 | OH | C3H7 | =O | napthoquinone | | =O | C16H14O5 | 286.283 |
| APX2029 | MeO | $CH=CR_2$ | $N(Et)_2$ | $C_3H_7$ | =O | napthoquinone | | =O | $C_{21}H_{25}NO_4$ | 355.434 |
| APX2030 | Me | $CH=CR_2$ | $N(Me)_2$ | $C_3H_7$ | =O | napthoquinone | | =O | $C_{19}H_{21}NO_3$ | 311.381 |
| APX2031 | MeO | $CH=CR_2$ | $NCH_3$ | $CH_3$ | =O | napthoquinone | | =O | $C_{16}H_{15}NO_4$ | 285.295 |
| APX2032 | MeO | $CH=CR_2$ | $N(CH_3)_2$ | $CH_3$ | =O | napthoquinone | | =O | $C_{17}H_{17}NO_4$ | 299.321 |
| APX2033 | MeO | $CH=CR_2$ | OH | $CH_3$ | =O | napthoquinone | | =O | $C_{15}H_{12}O_5$ | 272.253 |
| APX2034 | MeO | $CH=CR_2$ | OH | $C_3H_7$ | =O | napthoquinone | | =O | $C_{17}H_{16}O_5$ | 300.306 |
| APX2043 | MeO | $CH=CR_2$ | $N(CH_3)_2$ | $C_3H_7$ | OH | napthoquinone | | OH | $C_{19}H_{25}NO_4$ | 331.412 |
| APX2044 | $CF_3O$ | $CH=CR_2$ | $N(Et)_2$ | $C_3H_7$ | =O | napthoquinone | | =O | $C_{21}H_{22}F_3NO_4$ | 409.405 |
| APX2045 | $CH_3$ | $CH=CR_2$ | $N(Et)_2$ | $C_3H_7$ | =O | napthoquinone | | =O | $C_{21}H_{25}NO_3$ | 339.435 |
| APX2046 | $CH_3$ | $CH=CR_2$ | $N(Et)_2$ | $CF_3CH_2$ | =O | napthoquinone | | =O | $C_{21}H_{22}F_3NO_3$ | 393.406 |
| APX2047 | $CH_3$ | $CH=CR_2$ | $N(Et)_2$ | $C_3H_7$ | $OCH_3$ | napthoquinone | | $OCH_3$ | $C_{23}H_{31}NO_3$ | 369.505 |
| APX2048 | $CH_3$ | $CH=CR_2$ | $NOCH_3$ | $C_9H_{19}$ | =O | MeO | MeO | =O | $C_{23}H_{31}NO_4$ | 397.515 |
| APX2049 | $CH_3$ | $CH=CR_2$ | $N(CH_3)CC(O)C(O)C(O)C(O)COH$ | $C_9H_{19}$ | =O | MeO | MeO | =O | $C_{28}H_{45}NO_{10}$ | 555.665 |
| APX2050 | $CH_3$ | $CH=CR_2$ | $N(CH_3)OCH_3$ | $C_9H_{19}$ | =O | MeO | MeO | =O | $C_{23}H_{35}NO_6$ | 421.534 |

It has herein been found that the administration of APE1 inhibitors, and in particular, APX2009 and/or APX2014, inhibits APE1 protein from interacting with other proteins in the neurons. Particularly, APX2009 and APX2014 exert their antiangiogenic effects by blocking the activation of transcription factors induced by Ref-1, likely candidates including NF-κB and HIF-1α, both of which can regulate VEGF.

Suitable dosages of the APE1 inhibitor, pharmaceutically acceptable salts or pharmaceutically acceptable solvates thereof, for use in the methods of the present disclosure will depend upon a number of factors including, for example, age and weight of an individual, severity of ocular neovascularization-related disorder or disease to be treated, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

In one particularly suitable embodiment, the APE1/Ref-1 inhibitor is APX2009, and the subject is administered from about 12.5 mg/kg to about 35 mg/kg APX2009 per day.

In one particularly suitable embodiment, the APE1/Ref-1 inhibitor is APX2014, and the subject is administered from about 12.5 mg/kg to about 35 mg/kg APX2014 per day.

In some embodiments, the APE1 inhibitor is administered via a composition that includes the APE1 inhibitor and a pharmaceutically acceptable carrier. Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal), drop infusion preparations, or suppositories. These compositions can be prepared by conventional means, and, if desired, the active compound (e.g., APX2009, APX2014) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of the synthetic compounds into prodrugs, and the like for alleviating, mediating, preventing, and treating the diseases, disorders, and conditions described herein. For example, in one embodiment, the APE1 inhibitor can be administered with one or more of current therapeutic agents and drugs for treating ocular neovascularization (e.g., anti-VEGF therapies, including, for example, anti-VEGF biologics such as ranibizumab, bevacizumab, aflibercept; antisense RNA, RNA silencing or RNA interference (RNAi) of angiogenic factors, including ribozymes that target VEGF expression; inhibitors of the SRPK family of kinases, FOVISTA® and other agents targeting platelet derived growth factor (PDGF); squalamine ((1S,2S,5S,7R,9R,10R,11S,14R, 15R)—N-{3-[(4-aminobutyl)amino]propyl}-9-hydroxy-2, 15-dimethyl-14-[(2R,5R)-6-methyl-5-(sulfooxy)heptan-2-yl]tetracyclo[8.7.0.0^{2,7}.0^{11,15}]heptadecan-5-aminium); X-82 (Tyrogenix, Needham Heights, Mass.); PAN-90806 (PanOptica, Bernardsville, N.J.); TNP470 (Sigma-Aldrich, St. Louis, Mo.) and fumagillin (2E,4E,6E, 8E)-10-{[(3R,4S,5S,6R)-5-methoxy-4-[(2R)-2-methyl-3-(3-methylbut-2-enyl)oxiran-2-yl]-1-oxaspiro[2.5]octan-6- yl]oxy}-10-oxodeca-2,4,6,8-tetraenoic acid); protein kinase C inhibitors; inhibitors of VEGF receptor kinase; pigment epithelium derived factor (PEDF); endostatin; angiostatin; anecortave acetate; triamcinolone ((11β,16α)-9-Fluoro-11,16,17,21-tetrahydroxypregna-1,4-diene-3,20-dione); verteporfin (3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoic acid), porfimer sodium (photofrin)), vitamins and minerals (vitamins C and E, beta-carotene, zinc, copper, lutein, zeaxanthin, omega-3 fatty acids), and the like).

The pharmaceutical compositions including the APE1 inhibitor and/or pharmaceutical carriers used in the methods of the present disclosure can be administered to a subset of individuals/subjects in need. As used herein, a "subject in need" refers to an individual at risk for or having an ocular disease and/or ocular neovascularization, or an individual at risk for or having an ocular disease and/or a disease or disorder associated with ocular neovascularization (e.g., retinopathy of prematurity (ROP), proliferative diabetic retinopathy (PDR), diabetic retinopathy, wet age-related macular degeneration (AMD), pathological myopia, hypertensive retinopathy, occlusive vasculitis, polypoidal choroidal vasculopathy, diabetic macular edema, uveitic macular edema, central retinal vein occlusion, branch retinal vein occlusion, corneal neovascularization, retinal neovascularization, ocular histoplasmosis, neovascular glaucoma, retinoblastoma, and the like, and combinations thereof). Additionally, a "subject in need" is also used herein to refer to an individual at risk for or diagnosed by a medical professional as having ocular neovascularization or a disease or disorder related to ocular neovascularization. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of subjects "in need" of assistance in addressing one or more specific conditions noted herein), not all individuals will fall within the subset or subclass of individuals as described herein. In particular, the individual in need is a human. The individual in need can also be, for example, a research animal such as, for example, a non-human primate, a mouse, a rat, a rabbit, a cow, a pig, and other types of research animals known to those skilled in the art.

Unless defined otherwise, all technical and scientific terms used herein have the same meaning as commonly understood by one of ordinary skill in the art to which the disclosure belongs.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Example 1

In this Example, APX2009 and APX2014 were analyzed for their function on AP-1 DNA binding and cell proliferation and migration.

Materials and Methods

Synthetic Methods. The compounds were synthesized by Cascade Custom Chemistry (Eugene, Oreg.) and provided by Apexian Pharmaceuticals. In summary (FIG. 1A), iodolawsone (2-iodo-3-hydroxy-1,4 naphthoquinone) was made available from Cascade Custom Chemistry. HPLC were performed using an Alltech Alltima column C18 5u, 250×5 6 mm, flow 1 mL/min at 40° C. Elution was with a mobile phase of 15:10:75 water:A1:methanol where A1 was made using 700 mL of water, 300 mL methanol and 3 mL trimethylamine to which phosphoric acid was added to bring the pH to 3.4.

(E)-2-((3-hydroxy-1,4-dioxo-1,4-dihydronaphthalen-2-yl)methylene)pentanoic acid (3). In a 2 L 3-necked flask equipped with a mechanical stirrer and a gas dispersion fitted tube was placed 2-iodo-3-hydroxy-1,4 naphthoquinone, (iodolawsone, 1) (18 g, 0.06 mol) and 2-propylacrylic acid 2 (17.1 g, 0.15 mol) in a solution of potassium carbonate (41.4 g, 0.3 mol) in water (600 mL). The reaction mixture was stirred and sparged with argon for 30 minutes. Palladium(II) acetate (0.67 g, 0.003 mol) was added and sparging continued for an additional 30 minutes. The resulting mixture was heated in an oil-bath at 100° C. HPLC analysis showed the reaction was complete after 1 hour. The reaction mixture was cooled to room temperature and the black Pd metal was filtered. The filtrate was placed in a 2 L 3-necked flask equipped with a mechanical stirrer, cooled in an ice-methanol bath and acidified with 50% $H_3PO_4$ (160 mL) to pH 2. After stirring for 1 hour, the solid was collected, washed with water (1 L), a mixture of 20% acetone in water (500 mL), and air dried to give 12.3 g (72%) of (3) as a mustard colored solid. HPLC analysis showed a purity of 98%. NMR ($d_6$-DMSO) δ 12.6 (br s, 1H), 11.65 (br s, 1H), 8.0 (m, 2H), 7.8 (m, 2H), 7.15 (s, 1H), 2.1 (m, 2H), 1.4 (m, 2H), 0.8 (m, 3H).

(E)-2-((3-hydroxy-1,4-dioxo-1,4-dihydronaphthalen-2-yl)methylene)pentanoyl chloride (4). To a suspension of (3) (4.0 g, 0.014 mol) and DMF (0.1 mL) in dichloromethane (75 mL) was added oxalyl chloride (17.5 mL of 2M in $CH_2Cl_2$, 0.035 mol) over 20 minutes at room temperature. The resulting mixture was stirred at room temperature overnight and then was concentrated under reduced pressure to give 4.5 g (100%) (4) as a brown solid. This solid was used directly in the next step. NMR ($CDCl_3$) δ 7.8-8.2 (m, 2H), 7.7-7.8 (m, 2H), 7.4 (s, 1H), 2.1-2.4 (m, 2H), 1.2-1.7 (m, 2H), 0.6-1.0 (m, 3H).

(E)-N,N-diethyl-2-((3-chloro-1,4-dioxo-1,4-dihydronaphthalen-2-yl)methylene)pentanamide (5a). To a solution of crude (4) (9.7 g, 0.03 mol) in dichloromethane (50 mL) was a solution of diethylamine hydrochloride (4.97 g, 0.045 mol) and diisopropylamine (11.6 g, 0.09 mol) in dichloromethane (50 mL) at room temperature over 45 minutes. HPLC analysis after 15 minutes showed the reaction was complete. The reaction mixture was washed with water (100 mL), 1 M HCl (2×100 mL), and brine (100 mL). The organic phase was dried with 1PS paper and concentrated to a deep red solid. The solid was flash chromatographed over silica gel (150 g) with anhydrous sodium sulfate (20 g) on top packed with hexane. The column was eluted with 125 mL portions of 15% ethyl acetate in hexane for fractions 1-4, 25% ethyl acetate in hexane for fractions 5-8, 35% ethyl acetate in hexane for fractions 9-16, and 50% ethyl acetate in hexane for fractions 17-32. All fractions were checked by TLC (ethyl acetate:hexane; 1:1) and some fractions by HPLC. The product was eluted in fractions 21 to 30. They were combined and concentrated under reduced pressure to give an orange solid. This solid was suspended over 15% ethyl acetate in hexane (50 mL) and stirred for 15 minutes. The solid was collected and air dried to give 6.7 g (62%) of (5a) as an orange solid. HPLC analysis showed a purity of 99%. NMR (CDCl$_3$) δ 8.1-8.3 (m, 2H), 7.7-7.8 (m, 2H), 6.1 (s, 1H), 3.6 (br d, 4H), 2.2 (t, 2H), 1.45 (m, 2H), 1.25 (br s, (6H), 0.9 (t, 3H).

(E)-N-methoxy-2-((3-chloro-1,4-dioxo-1,4-dihydronaphthalen-2-yl)methylene)pentanamide (5b). To a solution of crude (4), prepared from (3) (20.0 g, 0.7 mol) with DMF (0.5 mL) in DCM (300 mL) and oxalyl chloride (2 M in DCM, 87.5 mL, 0.0175 mol), in 100 mL DCM and added to a solution of methoxyamine hydrochloride (7.0 g, 0.084 mol) and DIPEA (27.1 g, 0.21 mol) in DCM (100 mL) under argon and cooled in a room temperature water bath over 1 hour. After 30 minutes, HPLC indicated the reaction was complete. The mixture was washed with water (100 mL), 1 M HCl (100 mL), and brine (100 mL). The organic phase was dried with 1PS paper and concentrated to an orange oil. The crude oil was chromatographed on silica gel (350 g) with hexanes/EtOAc. The product eluted with 60% EtOAc/hexanes. The pure fractions were combined to give 19 g of an oil that solidified. The solid was triturated with hexanes (100 mL) and filtered to give 16.6 g of (5b) as a yellow solid (71%) at 98% purity.

(E)-N,N-diethyl-2-((3-methoxy-1,4-dioxo-1,4-dihydronaphthalen-2-yl)methylene)pentanamide (6a). To a solution of (5a) (5.0 g, 0.014 mol) in methanol (100 mL) was added a solution of sodium methoxide in methanol (4.2 mL of 5 M in MeOH) in one portion sparged with argon. After 30 minutes, HPLC indicated the reaction was complete. The reaction mixture was acidified to pH 3 by using 3 M HCl (3.5 mL), and then was concentrated under reduced pressure. The resulting residue was dissolved in ethyl acetate (150 mL), washed with water (2×75 mL), and brine (1×100 mL), filtered through 1PS filter paper and concentrated under reduced pressure to give an oil which solidified. This solid was triturated with hexane (50 mL) for 30 minutes and the solid was collected and air dried to give 4.8 g (96%) of (6a), APX2009, as a light orange solid. HPLC analysis showed a purity of 99%. NMR (CDCl$_3$) δ 8.15 (m, 2H), 7.75 (m, 2H), 6.2 (s, 1H), 4.1 (s, 3H), 3.6 (br d, 4H), 2.2 (t, 2H), 1.4 (m, 4H), 1.25 (br d, 4H), 0.85 (t, 3H).

(E)-N-methoxy-2-((3-methoxy-1,4-dioxo-1,4-dihydronaphthalen-2-yl)methylene)pentanamide (6b). To a solution of (5b) (10.0 g, 0.03 mol) in methanol (100 mL) was added a solution of sodium methoxide in methanol (9.0 mL of 5M in MeOH) in one portion sparged with argon. After 30 minutes, HPLC indicated the reaction was complete. The mixture was acidified to pH 2-3 with 3 M HCl. The mixture was concentrated under reduced pressure to a residue. The residue was dissolved in ethyl acetate (150 mL) and washed with water (100 mL) and brine (100 mL). The organic phase was dried over 1PS paper and concentrated under reduced pressure to an oil that solidified. The solid was triturated with hexanes (150 mL) for 30 minutes and filtered to give 8.7 g (83%) of (6b), APX2014, as a yellow solid. HPLC analysis showed a purity of 99%. NMR (CDCl$_3$) δ 8.8 (br s, 1H), 8.1 (m, 2H), 7.75 (m, 2H), 6.7 (s, 1H), 4.15 (s, 3H), 3.9 (s, 3H), 2.2 (m, 2H), 1.4 (m, 2H), 0.85 (t, 3H).

APX3330 was synthesized as described in Luo et al., *Antioxid Redox Signal* 10:18531867 (2008).

Electrophoretic mobility shift assays (EMSA). These assays were performed as previously described (Luo et al., *Antioxid Redox Signal* 10:18531867 (2008); Kelley et al., *Antioxid Redox Signal* 14:1387-1401 (2011); Su et al., *Biochemistry* 50:82-92 (2011); Luo et al., *Biochemistry* 51:695-705 (2012); Zhang et al., *Biochemistry* 52:2955-2966 (2013)). Briefly, an increasing amount of APX3330, APX2009 or APX2014 was pre-incubated with purified Ref-1 protein in EMSA reaction buffer for 30 minutes. The EMSA assay was performed using the AP-1 target DNA sequence and AP-1 protein.

Cells. Primary human retinal microvascular endothelial cells (HRECs) were obtained from Cell Systems, Inc. (Kirkland, Wash.), while the Rf/6a macacque choroidal endothelial cell line was obtained from ATCC (Manassas, Va.). Cells were maintained as described (Basavarajappa et al., *EMBO Mol Med* 9:786-801 (2017)), re-ordered at least annually, and regularly assessed for *mycoplasma* contamination.

In vitro cell proliferation assay. Endothelial cell proliferation was measured as described previously (Basavarajappa et al., *PLoS One* 9:e95694 (2014); Basavarajappa et al., *EMBO Mol Med* 9:786-801 (2017)). Briefly, 2.5×10$^3$ cells were seeded in 100 µL of growth medium and plated in each well of 96-well clear-bottom black plates and incubated for 24 hours. APX2009, APX2014, or DMSO vehicle (DMSO final concentration=1%) was added, and the plates were incubated for 24-48 hours in 100 µL complete medium at 37° C. and 5% CO$_2$. AlamarBlue reagent (11.1 µL) was added to each well of the plate and 4 hours later fluorescence readings were taken at excitation and emission wavelengths of 560 nm and 590 nm, respectively, using a Synergy H1 plate reader (BioTek, Winooski, Vt.). GI50 was calculated using GraphPad Prism v. 7.0.

EdU incorporation, Ki-67 Staining and TUNEL. These assays were carried out as described previously (Basavarajappa et al., *PLoS One* 9:e95694 (2014); Basavarajappa et al., *EMBO Mol Med* 9:786-801 (2017)) with the exception of using chamber slides, not coverslips. Briefly, cells (30,000 per well) were seeded on 8-well chamber slides coated with attachment factors and allowed to attach overnight. Cells were treated with the indicated compound concentrations for 17 hours (overnight). To assay proliferation, cells were incubated with EdU in complete media for 8 hours at 37° C. Cells were then fixed in 4% paraformaldehyde for 20 minutes and permeabilized using 0.25% Triton X-100 prepared in PBS. Cells were incubated with a rabbit-specific monoclonal antibody against Ki-67 (D3B5) (#9129; Cell Signaling, Danvers, Mass.) (1:400) overnight at 4° C. Secondary antibody was Alexa Fluor goat anti-rabbit 488 (A11034; Invitrogen, Carlsbad, Calif.) with DAPI counter-stain for nuclear staining. Proliferating cells that incorporated EdU were detected using the Click-iT EdU Imaging kit (Invitrogen, Carlsbad, Calif.). Alternatively, apoptotic cells were visualized using the Click-iT TUNEL assay kit (Invitrogen, Carlsbad, Calif.) as per the manufacturer's instructions, with Hoechst 33342 counter-stain for nuclear staining, and a 17-hour treatment with 1 µM staurosporine as positive control. The cells were imaged using a Zeiss AxioImager D2 microscope or an LSM 700 confocal microscope and the percentage of positive cells was counted on three low-power (for TUNEL) or high-power (for Ki-67 and EdU) fields per well using ImageJ software.

Cell cycle analysis. HRECs (2×10$^6$) were grown in EGM-2 medium. Cells were serum starved in EBM-2 medium overnight, then treated with the indicated concentrations of APX2009 or APX2014 along with DMSO control for 24 hours in complete medium. Cells were washed twice in ice-cold PBS followed by fixation in 66% ethanol solution overnight at 4° C. Fixed cells were again washed twice in ice-cold PBS and the pellets were resuspended in propidium iodide staining solution for 30 minutes at 37° C. (20 µg/mL propidium iodide prepared in 1×PBS containing 0.1% Triton X-100 and 100 µg/mL RNase A). After incubation cells were analyzed using flow cytometry (FACSCalibur, BD Biosciences, San Jose, Calif.). Pulse shape analysis was used to exclude doublets and debris. The single cell population was then assessed by the FL2 area histogram plot using ModFit software (v. 5.0) and cell cycle profiles were generated.

In vitro cell migration assay. Endothelial cell migration was monitored as described before (Basavarajappa et al., *PLoS One* 9:e95694 (2014); Basavarajappa et al., *EMBO Mol Med* 9:786-801 (2017)). Briefly, HRECs and Rf/6a were grown until confluency in 12-well plates. Using a sterile 10-µL micropipette tip, a scratch wound was made across the center of each well and fresh complete media containing DMSO or different concentrations of APX2009 or APX2014 compounds were added to the wells (DMSO final concentration=1%). Wells were imaged via digital brightfield microscopy at different time points, and the number of migrated cells into the scratched area was manually counted.

In vitro Matrigel tube formation assay. The ability of HRECs and Rf/6a cells to form tubes in vitro was monitored as described before (Basavarajappa et al., *PLoS One* 9:e95694 (2014); Basavarajappa et al., *EMBO Mol Med* 9:786-801 (2017)). Briefly, cells were treated with the indicated concentrations of APX2009 or APX2014 compounds or DMSO for 48 hours and then $1.5 \times 10^4$ cells in 100 µL of growth medium containing DMSO or APX compounds were added to each well of a 96-well plate that was pre-coated with 50 µL of Matrigel basement membrane (DMSO final concentration=1%). Digital photographs of each well at different time points were taken to measure the in vitro tube formation using the Angiogenesis Analyzer plugin in ImageJ software (v.1.48; http://image.bio.methods.free.fr/ImageJ/?Angiogenesis-Analyzer-for-ImageJ.html).

NF-κB p65 nuclear translocation assay. The NF-κB nuclear translocation assay was performed by seeding 30,000 HRECs/well on an 8-well chamber slide coated with attachment factors. The cells were grown in EGM-2 medium overnight before treating with indicated concentrations of APX2009 and APX2014, or 10 µM BAY 11-7082 (Sigma, St. Louis, Mo.) as a positive control NF-κB inhibitor. After 17 hours incubation, the media was replaced with EBM-2 (minimal medium) with indicated concentrations of compound or DMSO for 1 hour. The cells were then stimulated with 10 ng/ml TNF-α in EBM-2 for 20 minutes at 37° C. to activate NF-κB. Cells were then fixed in 4% paraformaldehyde and permeabilized using 0.5% Triton X-100 solution prepared in PBS. The cells were incubated with a monoclonal antibody against NF-κB p65 (sc-8008; Santa Cruz, Santa Cruz, Calif.) (1:50) overnight at 4° C., followed by Alexafluor 555 goat anti-mouse secondary antibody (1:2000) for one hour. The cells were counter-stained with Hoechst 33342 for nuclear staining and then mounted using Everbrite hardset mounting medium. The cells were imaged using a Zeiss AxioImager D2 microscope.

qRT-PCR. The assay was performed as described previously (Basavarajappa et al., *PLoS One* 9:e95694 (2014); Basavarajappa et al., *EMBO Mol Med* 9:786-801 (2017)). RNA was extracted from cells treated as indicated using Trizol (Invitrogen). cDNA was synthesized from 1 µg RNA using random primers and iScript reverse transcriptase (Bio-Rad, Hercules, Calif.). qPCR was performed in 10 µL volumes in a 384-well plate, with Fast Advanced Master Mix and TaqMan probes on a ViiA7 thermal cycler (Applied Biosystems, Foster City, Calif.). Primer/probesets used were as follows: VEGFA (Hs00900055_m1), VCAM1 (Hs01003372_m1), and CCL20 (Hs01011368_m1), and housekeeping controls HPRT (Hs02800695_m1) and TBP (Hs00427620_m1). The data were analyzed using the ΔΔCt method. The expression levels of genes were normalized to the two housekeeping genes and calibrated to the DMSO treated sample.

Animals. All animal experiments were approved by the Indiana University School of Medicine Institutional Animal Care and Use Committee and followed the guidelines of the Association for Research in Vision and Ophthalmology Statement for the Use of Animals in Ophthalmic and Visual Research. Wild-type female C57BL/6 mice, 6-8 weeks of age, were purchased from Envigo (Indianapolis, Ind.; for choroidal sprouting experiments) or Jackson Laboratory (Bar Harbor, Me.; for L-CNV) and housed under standard conditions (Wenzel et al., *Mol Vis* 21:515-522 (2015)). Mice were anesthetized for all procedures by intraperitoneal injections of 90 mg/kg ketamine hydrochloride and 5 mg/kg xylazine, with intraperitoneal atipamezole reversal (1 mg/kg). Treatments were randomly assigned by cage.

Choroidal sprouting assay. Ex vivo Choroidal sprouting was assessed as described previously (Sulaiman et al., *Sci Rep* 6:25509 (2016); Basavarajappa et al., *EMBO Mol Med* 9:786-801 (2017)). Briefly, choroid-sclera was dissected from 7 to 8 week old mouse eyes and pieces were embedded in Matrigel (growth factor reduced) and grown in EGM-2 medium containing antibiotics for 72 hours to allow sprouting to initiate. The indicated concentrations of APX2009 and APX2014 compounds (in DMSO, final DMSO concentration 0.5 and 0.2%, respectively) were added and growth allowed to proceed for 48 hours Images were taken and growth was quantified by measuring the distance from the edge of the choroidal piece to the growth front in four directions per sample using ImageJ software.

Laser-induced choroidal neovascularization. L-CNV was induced as described previously (Sulaiman et al., *J Ocul Pharmacol Ther* 31:447-454 (2015); Sulaiman et al., *Sci Rep* 6:25509 (2016); Basavarajappa et al., *EMBO Mol Med* 9:786-801 (2017)). Studies were powered to have an 80% chance of detecting effect size differences of 50%, assuming 30% variability, $\alpha=0.05$. Briefly, pupils of anesthetized mice were dilated with 1% tropicamide (Alcon Laboratories Inc., Fort Worth, Tex.) and lubricated with hypromellose ophthalmic demulcent solution (Gonak) (Akorn, Lake Forest, Ill.). A coverslip was used to allow viewing of the posterior pole of the eye. Three burns of a 532 nm ophthalmic argon green laser coupled with a slit lamp (50 µm spot size, 50 ms duration, and 250 mW pulses) were delivered to each 3, 9, and 12 o'clock position, two-disc diameters from optic disc. The bubbling or pop sensed after laser photocoagulation was considered as the successful rupture of Bruch's membrane. Lesions in which bubbles were not observed were excluded from this Example. To assess the antiangiogenic activity of APX3330, the mice were i.p. injected with compound (50 mg/kg body weight), twice daily, five days on/two days off, as used previously in vivo (Fishel et al., *Mol Cancer Ther* 10:1698-1708 (2011); Lou et al., *Oncol Lett* 7:1078-1082 (2014); Biswas et al., *Am J Physiol Cell Physiol* 309:C296-307 (2015)). Vehicle was 42% Cremophor: 2% ethanol in PBS. For APX2009, doses were 12.5 mg/kg or 25 mg/kg body weight, twice daily until 14 days of laser treatment unless otherwise indicated. Vehicle was propylene glycol, Kolliphor HS15, Tween 80 (PKT) (McIlwain et al., *Oncotarget* doi.org/10.18632/oncotarget.23493. (2017)). Mice were weighed daily.

In vivo imaging. Optical coherence tomography (OCT) was performed in L-CNV mice as described previously (Sulaiman et al., *Sci Rep* 6:25509 (2016)), at the indicated times using the Micron III intraocular imaging system (Phoenix Research Labs, Pleasanton, Calif.). Briefly, before the procedure, eyes of anesthetized mice were dilated with 1% tropicamide solution (Alcon, Fort Worth, Tex.) and lubricated with hypromellose ophthalmic demulcent solution (Gonak) (Akorn, Lake Forest, Ill., USA). Mice were then placed on a custom heated stage that moves freely to position the mouse eye for imaging Several horizontal and vertical OCT images were taken per lesion. Fluorescein angiography was performed 14 days post laser by intraperitoneal injection of 50 µL of 25% fluorescein sodium (Fisher Scientific, Pittsburgh, Pa.). Fundus images were taken using the Micron III system and Streampix software.

Choroidal flatmount immunofluorescence. Mouse eyes were harvested 14 days after L-CNV induction. The eyes were enucleated and fixed in 4% paraformaldehyde/PBS overnight. The anterior segment, lens, and retina were removed, and the posterior eye cups were prepared for choroidal flat mounts. The posterior eye cups were washed with PBS and permeabilized in blocking buffer containing 0.3% Triton X-100, 5% bovine serum albumin (BSA) in PBS for two hours at 4° C. After blocking, the eye cups were double stained for vasculature with rhodamine-labeled *Ricinus communis* agglutinin I (Vector Labs, Burlingame, Calif.) and Alexa Fluor™ 488 conjugated-Isolectin B4 from *Griffonia simplicifolia* (GS-IB4) (Molecular Probes, Thermo Fisher Scientific) at 1:250 concentration in buffer containing 0.3% Triton X-100, 0.5% BSA in PBS for 16-20 hours at 4° C. After antibody incubation, whole mounts were washed three times with PBS for 15 minutes each step at 4° C. with 0.1% Triton X-100. After washing, choroidal flatmounts were mounted in aqueous mounting medium (VectaShield; Vector Laboratories, Inc.) and cover-slipped for observation by confocal Z-stack imaging (LSM 700, Zeiss, Thornwood, N.Y.) to estimate lesion volume. The sum of the stained area in each optical section, multiplied by the distance between sections (3 µm), gave the CNV lesion volume and lesion volume was quantified using ImageJ software. Lesions were only included for analysis if they met quality control standards as published (Poor et al., *Invest Ophthalmol Vis Sci* 55:6525-6534 (2014)). All lesions in an eye were averaged to represent a single n.

Statistical analyses. Statistical analyses were performed with GraphPad Prism 7 software. One-way ANOVA was used with Dunnett's post hoc test for migration, tube formation, and choroidal sprouting experiments. One-way ANOVA was used with Tukey's post hoc test for APX2009 in vivo experiments. Unpaired Student's t-test was used for the APX3330 in vivo experiment. Two-sided p values <0.05 were considered statistically significant.

Results

Figure 1B:
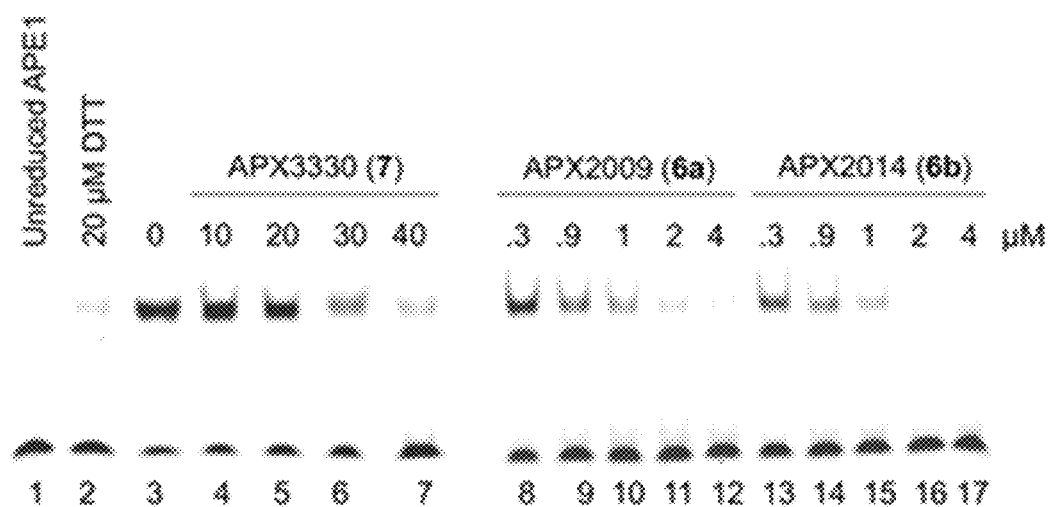
Figure 2A:
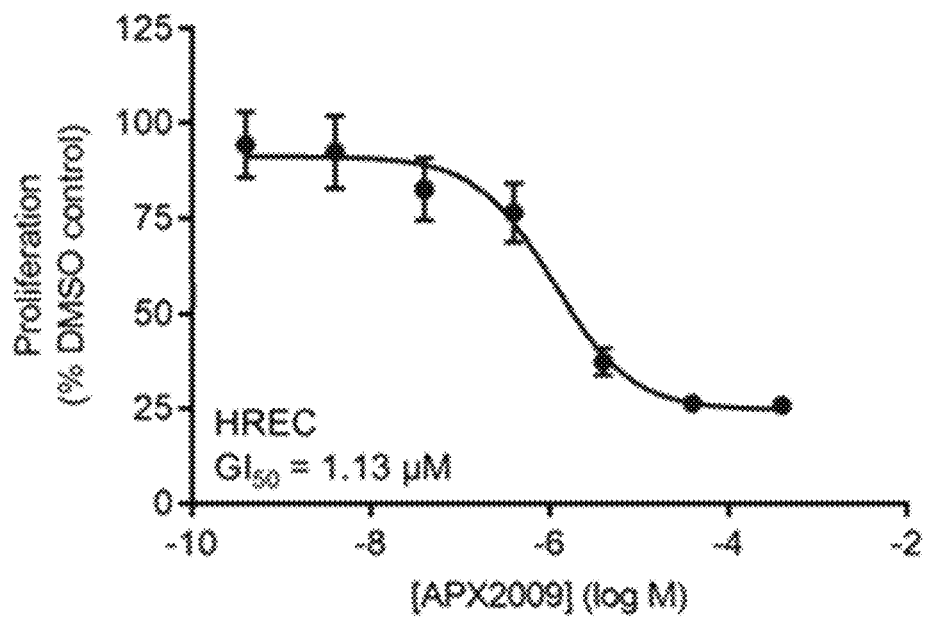
FIGS. 2A-2D depict compounds APX2009 and APX2014 inhibit endothelial cell proliferation in HRECs and Rf/6a cells in vitro. Dose dependent effects of APX2009 (FIG. 2A) and APX2014 (FIG. 2B) in human retinal endothelial cells (HRECs), and dose dependent effects of APX2009 (FIG. 2C) and APX2014 (FIG. 2D) in Rf/6a choroidal endothelial cells. In vitro proliferation was measured using an alamarBlue assay. Median growth inhibition ($GI_{50}$) values are indicated. Mean±S.E.M., n=3 per dose.
Figure 2B:
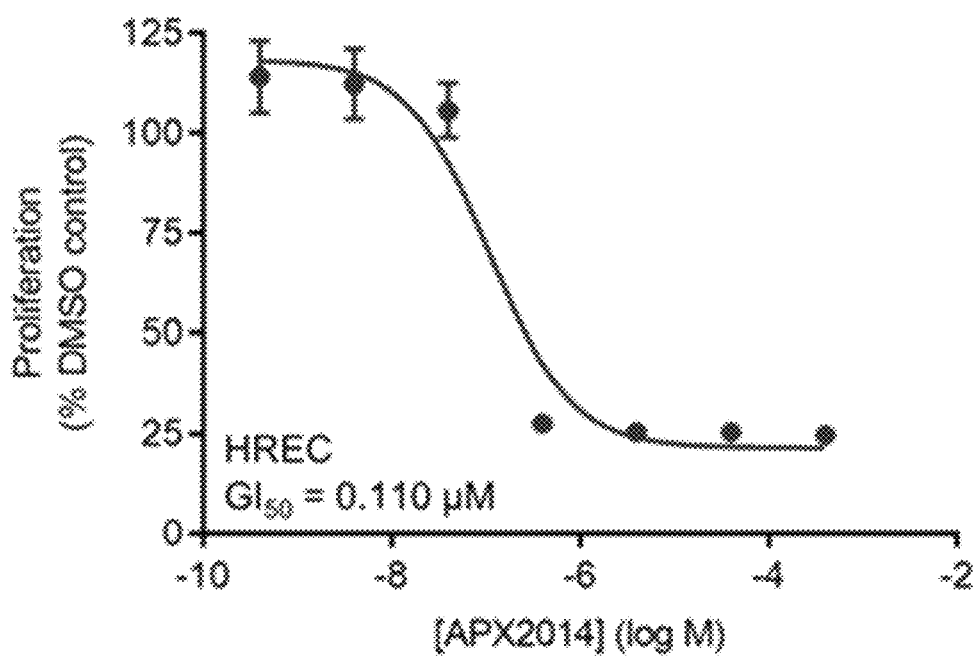
Figure 2C:
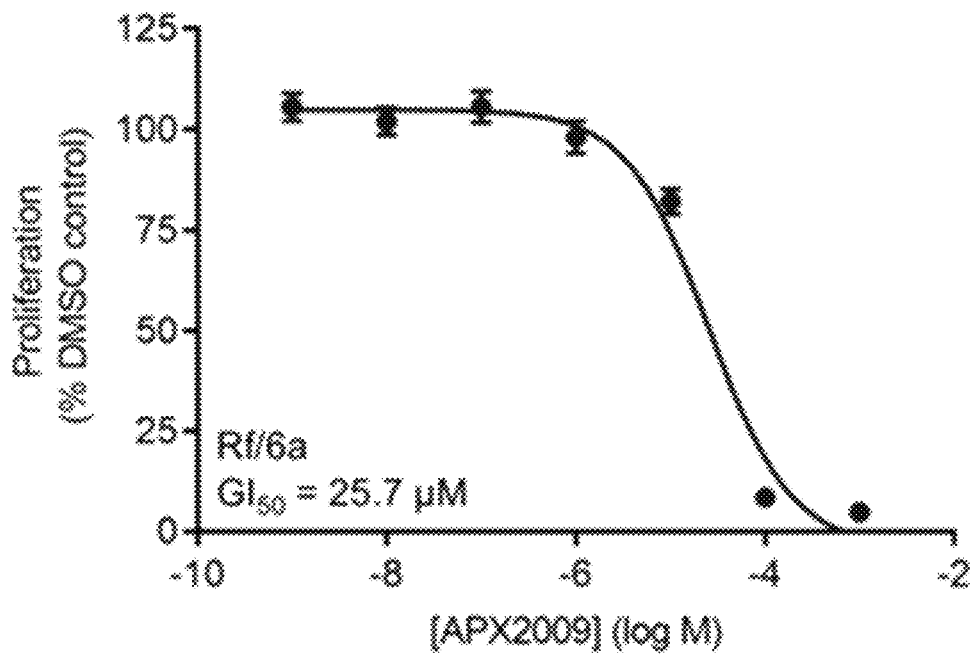
Figure 2D:
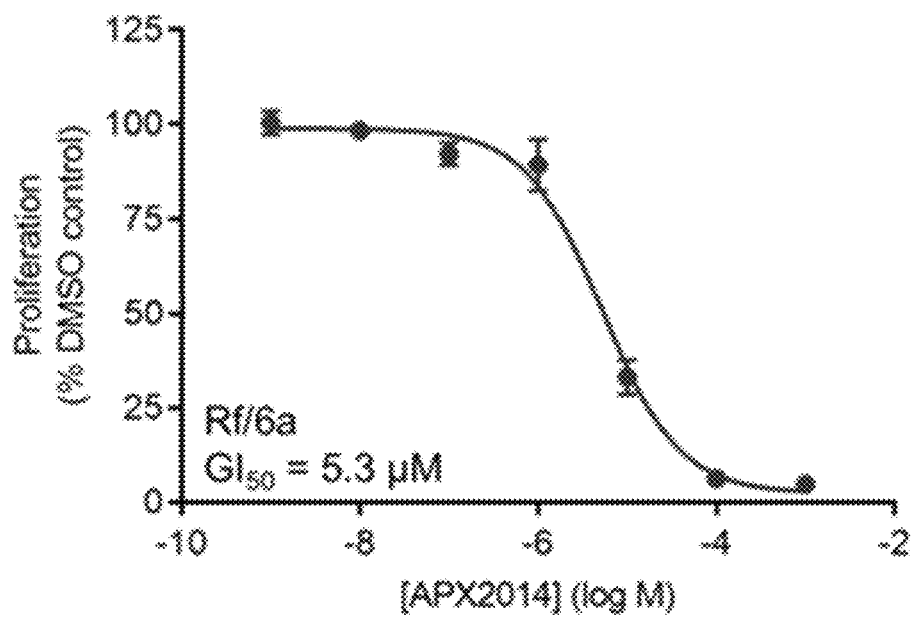
Figure 3A:
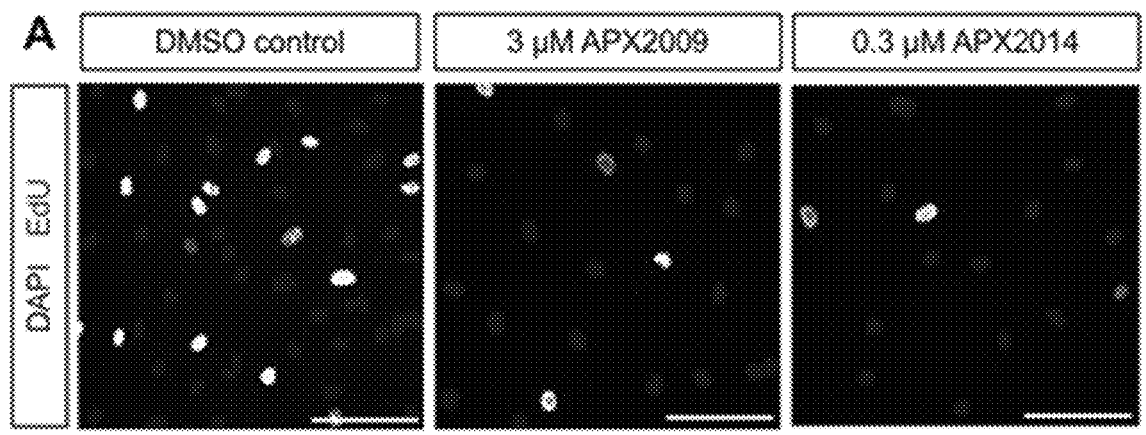
FIGS. 3A-3D depict compounds APX2009 and APX2014 inhibit S phase in HRECs. After treating HRECs with the indicated concentrations of APX2009 and APX2014, (FIG. 3A) EdU (red) and (FIG. 3C) Ki-67 (green) were detected and nuclei (blue) stained with DAPI; Scale bar=100 μm.
Figure 3B:
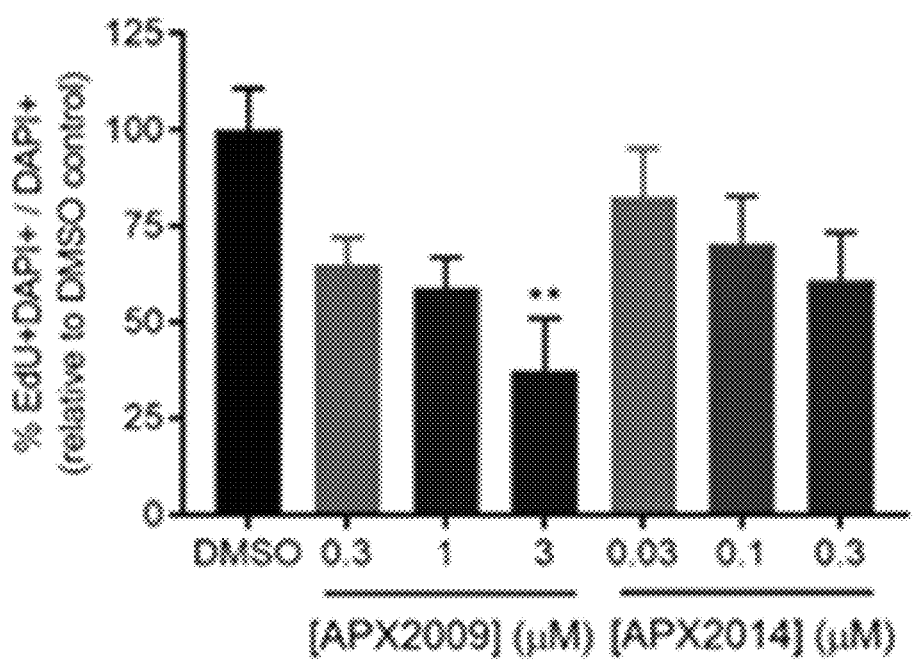
Figure 3C:
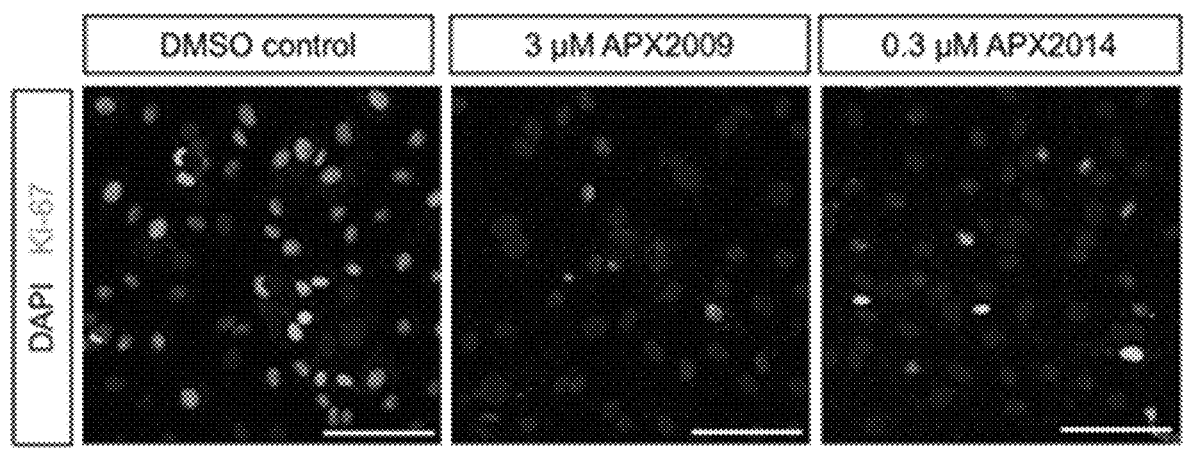
Figure 3D:
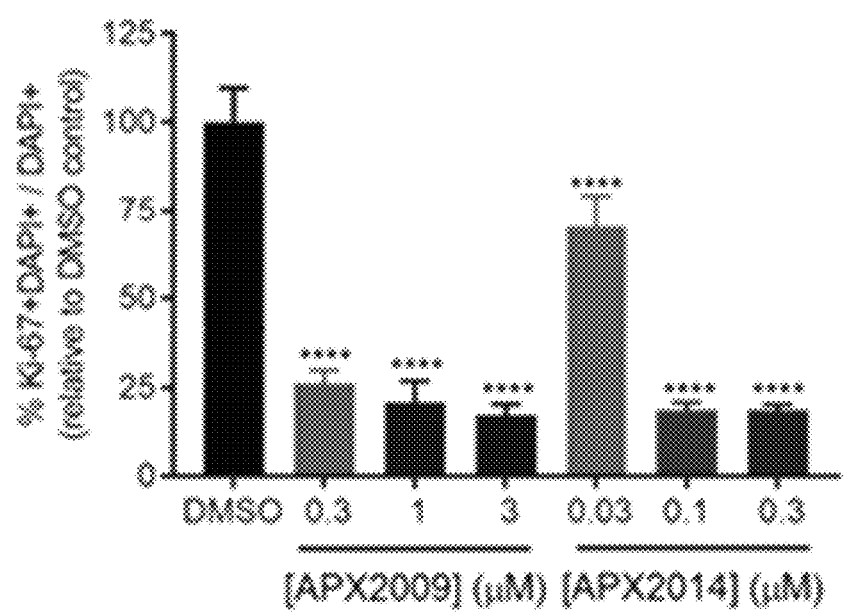

Ref-1 inhibitors APX2009 and APX2014 were more potent than APX3330. APX2009 (6a) and APX2014 (6b) (FIG. 1A) was synthesized and demonstrated that both compounds had enhanced inhibition of Ref-1-induced transcription factor binding to DNA compared to APX3330 (7) (FIG. 1B), while having substantially different physiochemical properties. The new compounds have lower molecular weights, and lack the carboxylate group and long alkyl chain of APX3330. The new compounds also have significantly reduced lipophilicity as determined by computer based calculation of their c log P values, APX3330=4.5, APX2009=2.7, and APX2014=1.9.

APX2009 and APX2014 blocked endothelial cell proliferation. Endothelial cell proliferation with increased survival supports the cells that make up new blood vessels, leading to angiogenesis. Proliferation assays were carried out to measure angiogenic or antiangiogenic activity. As an initial test of the antiangiogenic potential of our these two new Ref-1 inhibitors, their ability to inhibit the proliferation of HRECs and Rf/6a choroidal endothelial cells (FIGS. 2A-2D) was assessed. Both compounds dose-dependently blocked proliferation of both cell types in an alamarBlue assay, with APX2014 more potent than APX2009. Primary HRECs were more sensitive to both compounds than the Rf/6a choroidal cell line, as seen for other antiangiogenic compounds.

Figure 4A:
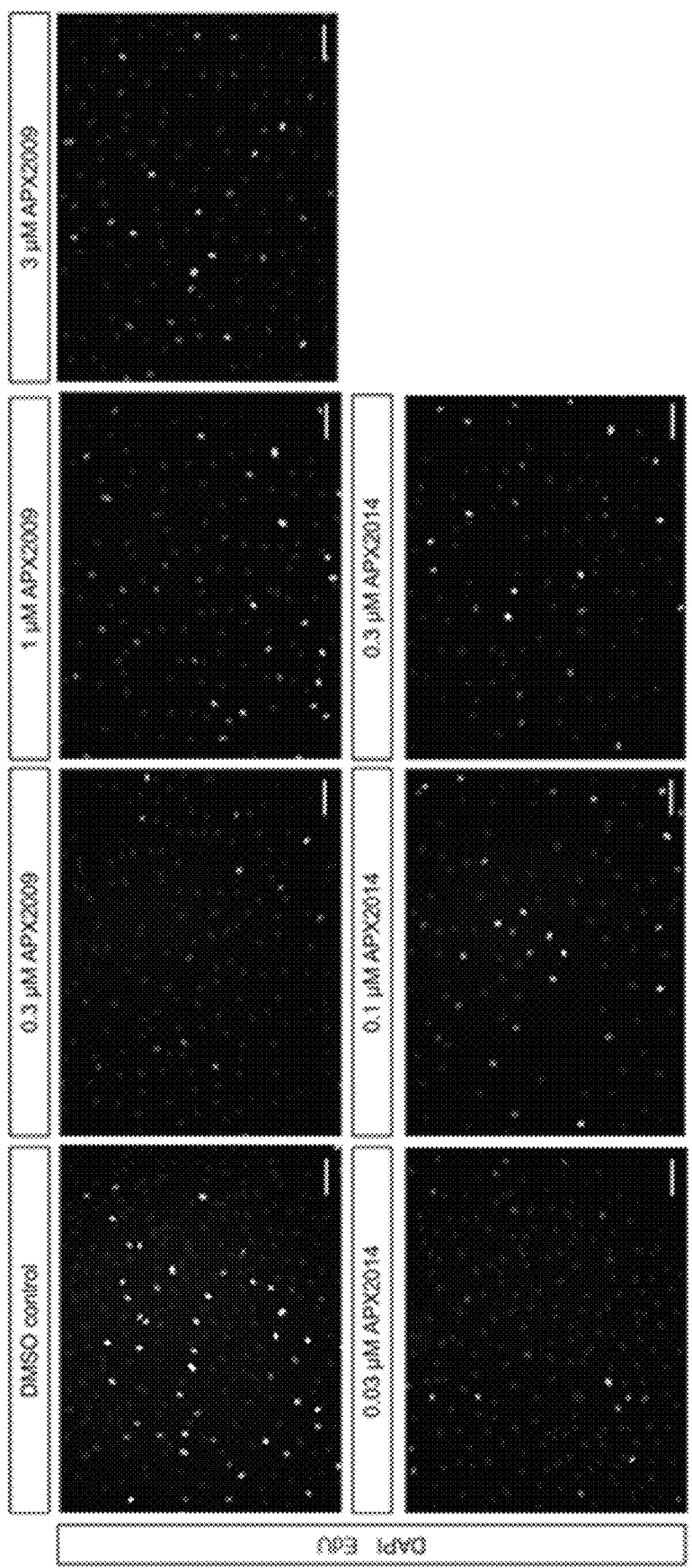
FIG. 4A depicts full fields of the EdU staining for all doses (same experiment as FIGS. 3A-3D) show that APX2009 and APX2014 decreased DNA synthesis dose dependently in HRECs. Scale bars=100 μm.
Figure 4B:
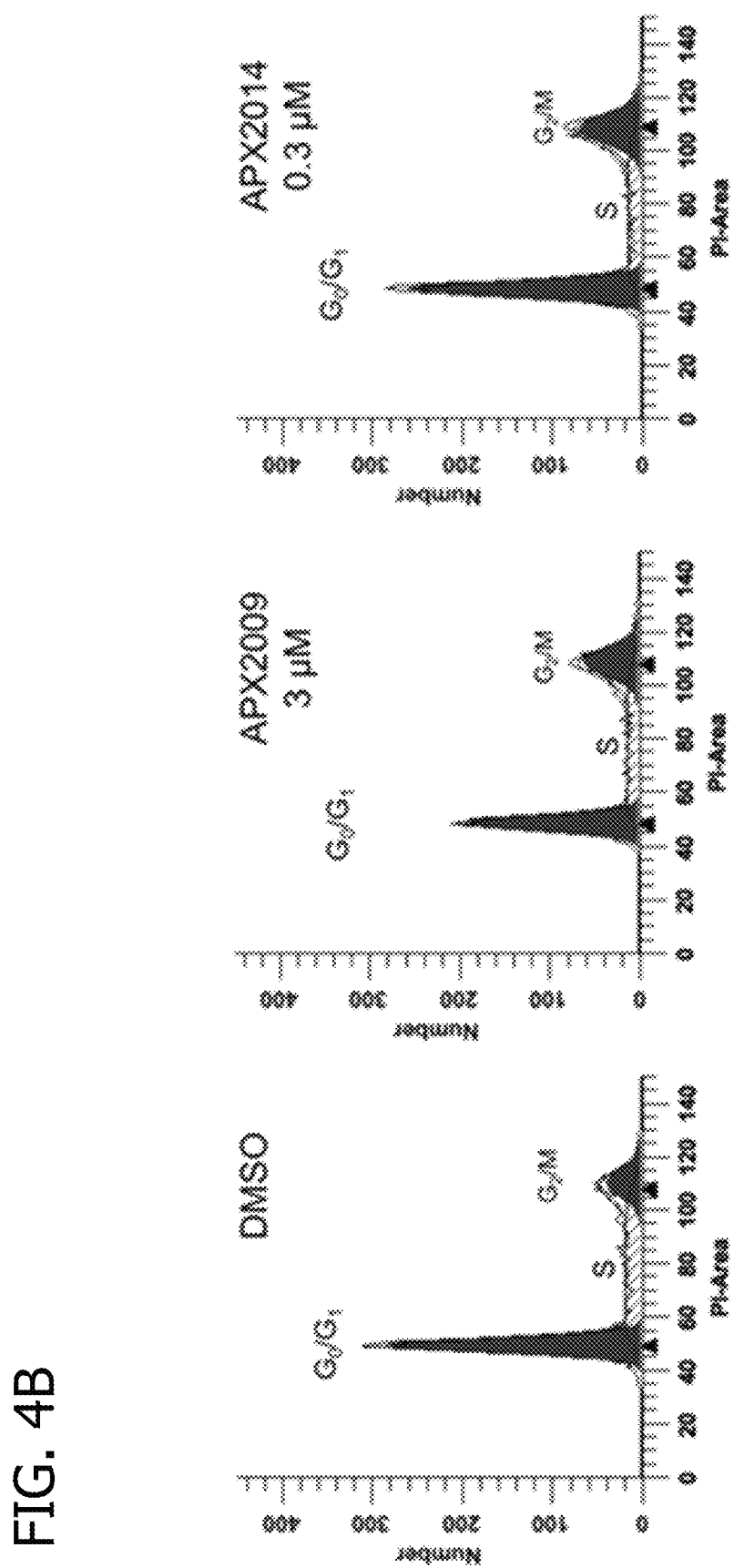
FIG. 4B depicts propidium iodide cell cycle profiles for indicated treatments.
Figure 4C:
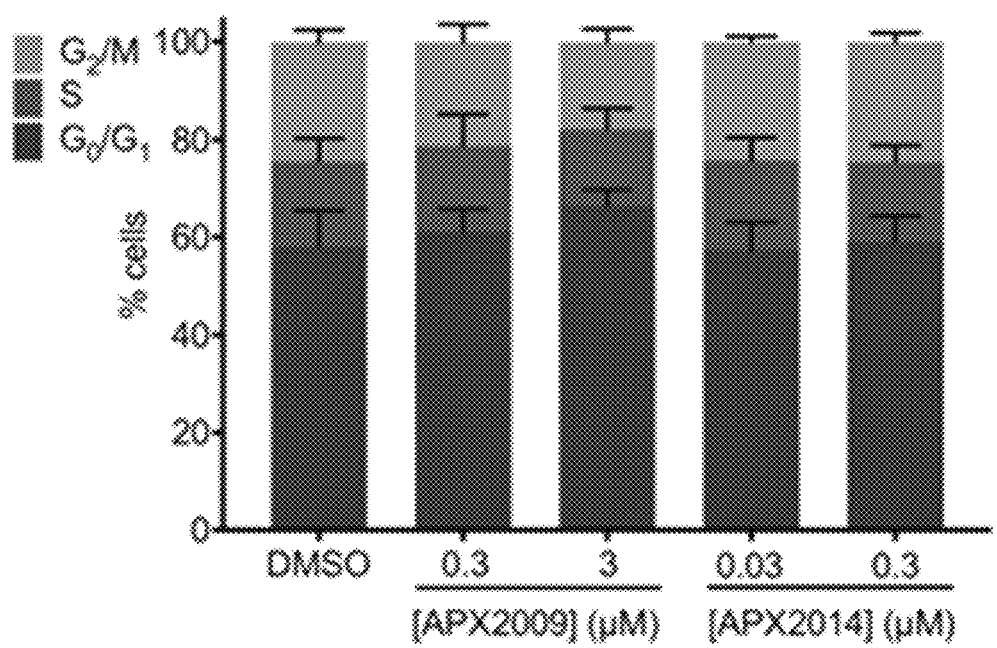
FIG. 4C shows quantification of cell cycle phase. Mean±S.E.M., n=3 independent experiments.
Figure 5:
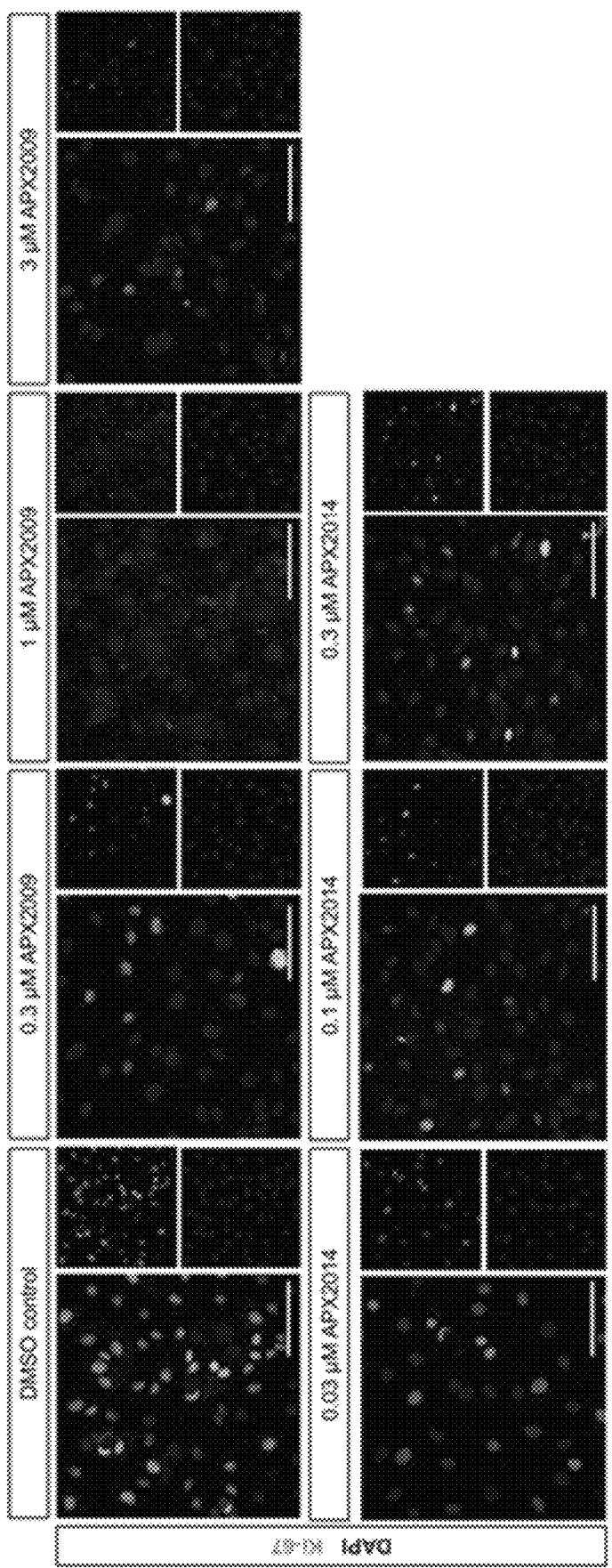
FIG. 5 depicts separate channel images of Ki-67 staining for all doses (same experiment as FIGS. 3A-3D) show that APX2009 and APX2014 decreased proliferation dose dependently in HRECs. Scale bars=100 μm.
Figure 6A:
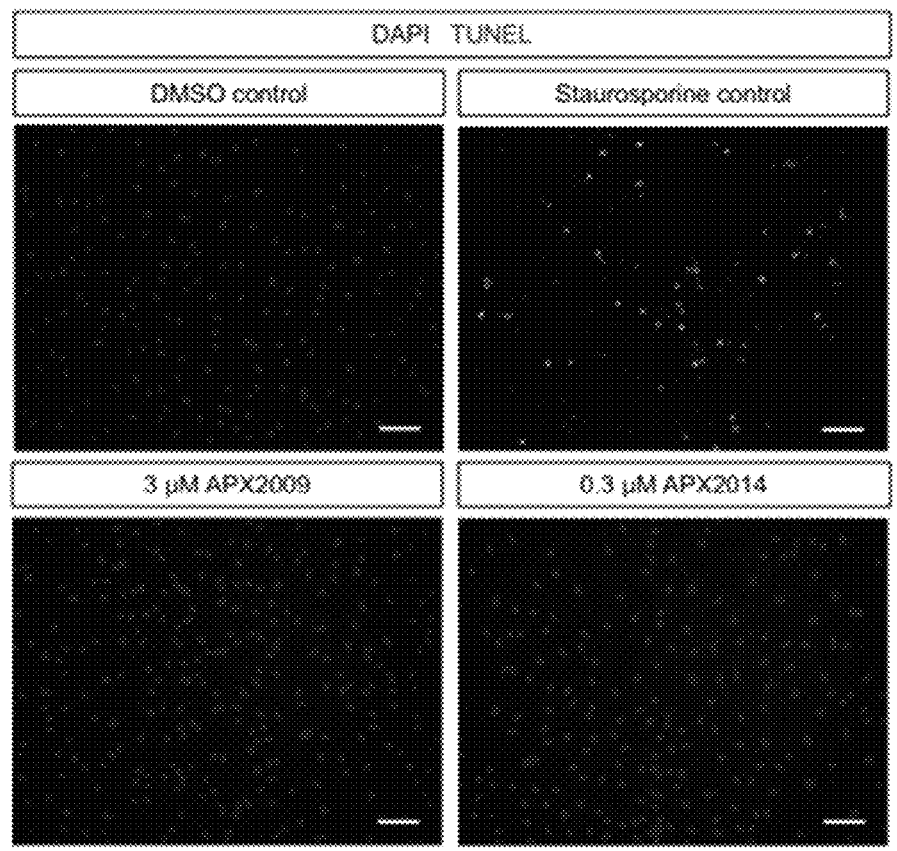
FIGS. 6A & 6B depict that APX2009 and APX2014 did not induce cell death in HRECs.
Figure 6B:
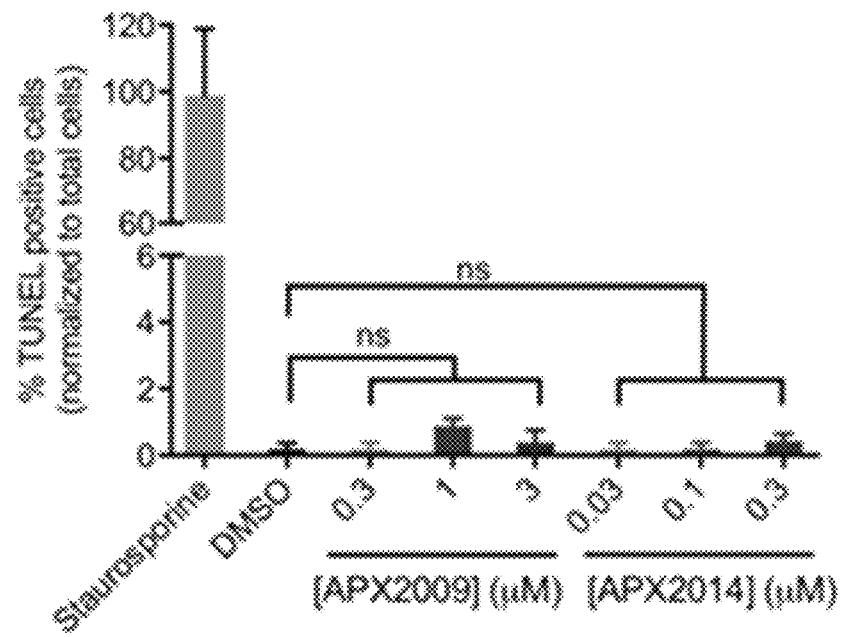
Figure 7A:
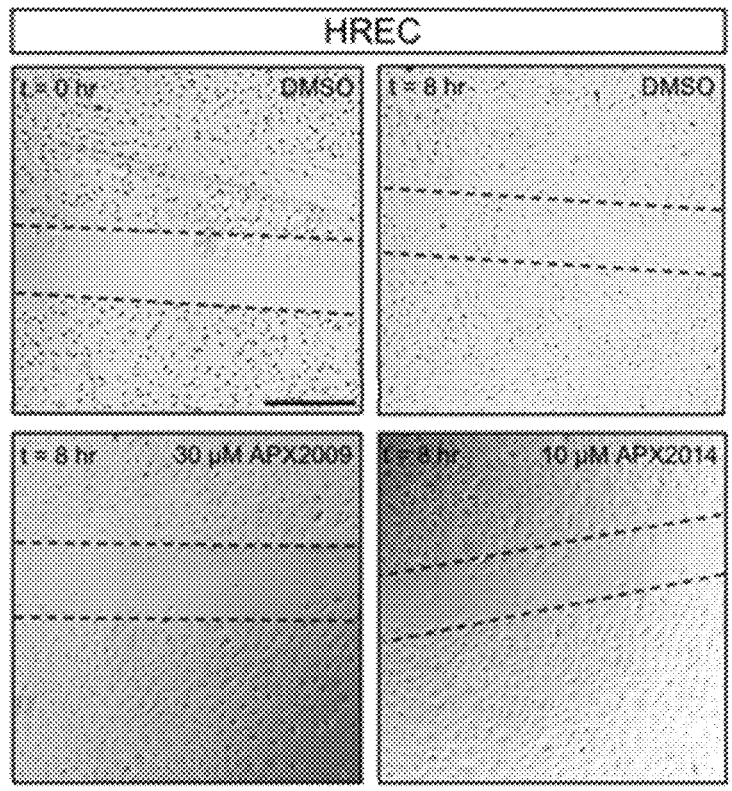
FIGS. 7A-7D show that compounds APX2009 and APX2014 inhibited endothelial cell migration in HRECs and Rf/6a cells in vitro.
Figure 7B:
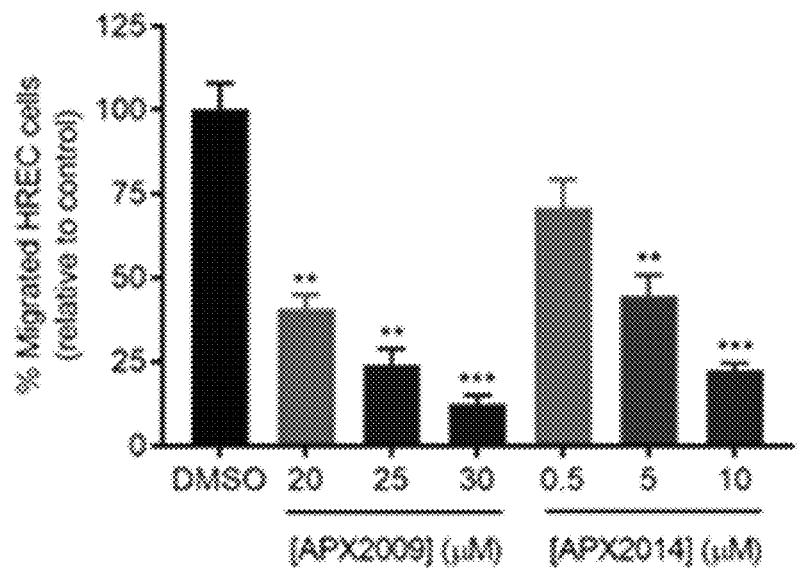
Figure 7C:
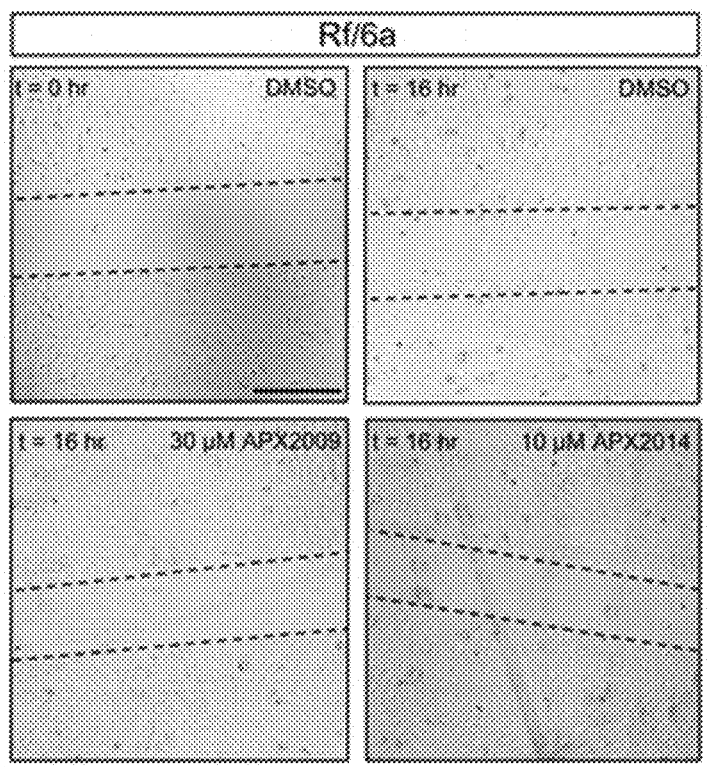
Figure 7D:
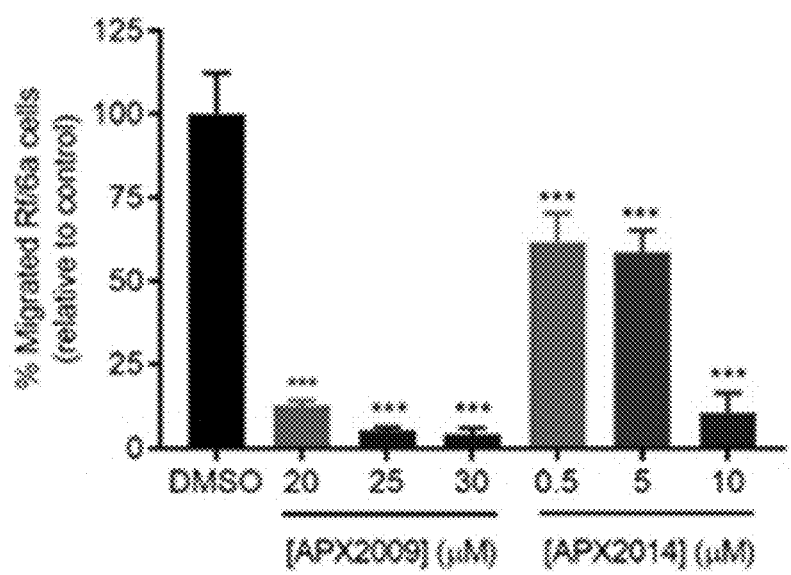
Figure 8A:
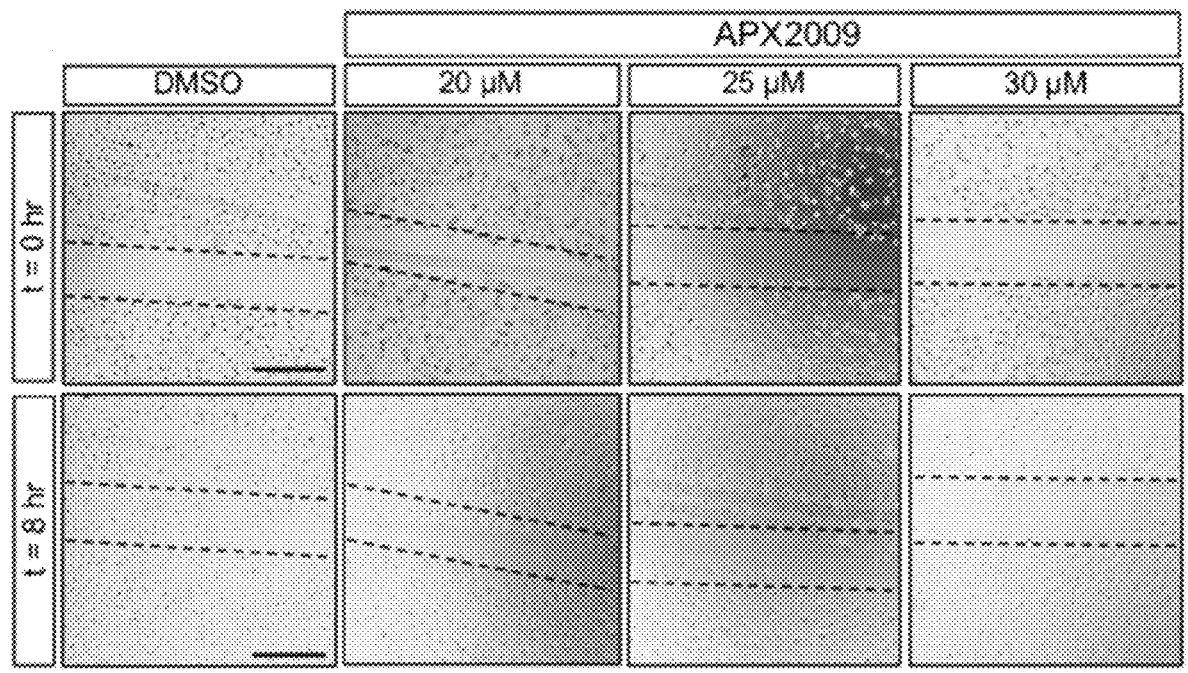
FIGS. 8A-8D depict APX2009 and APX2014 inhibited migration of HRECs and Rf/6a cells in vitro. The effect of (FIG. 8A) APX2009 and (FIG. 8B) APX2014 on cell migration in HRECs is shown. A confluent monolayer of HRECs treated with various concentrations of each compound was wounded and wound closure was monitored for 8 hours. The effect of (FIG. 8C) APX2009 and (FIG. 8D) APX2014 on cell migration in Rf/6a cells is shown. A confluent monolayer of Rf/6a cells treated with various concentrations of each compound was wounded and wound closure was monitored for 16 hours. Scale bars=500 μm.
Figure 8B:
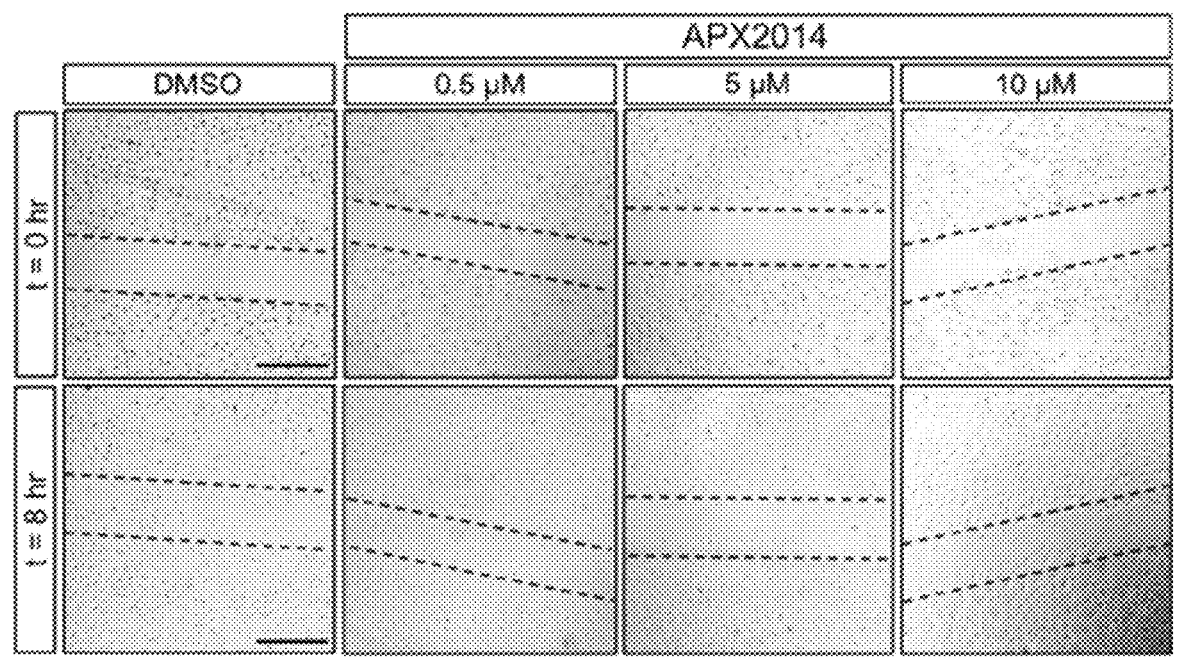
Figure 8C:
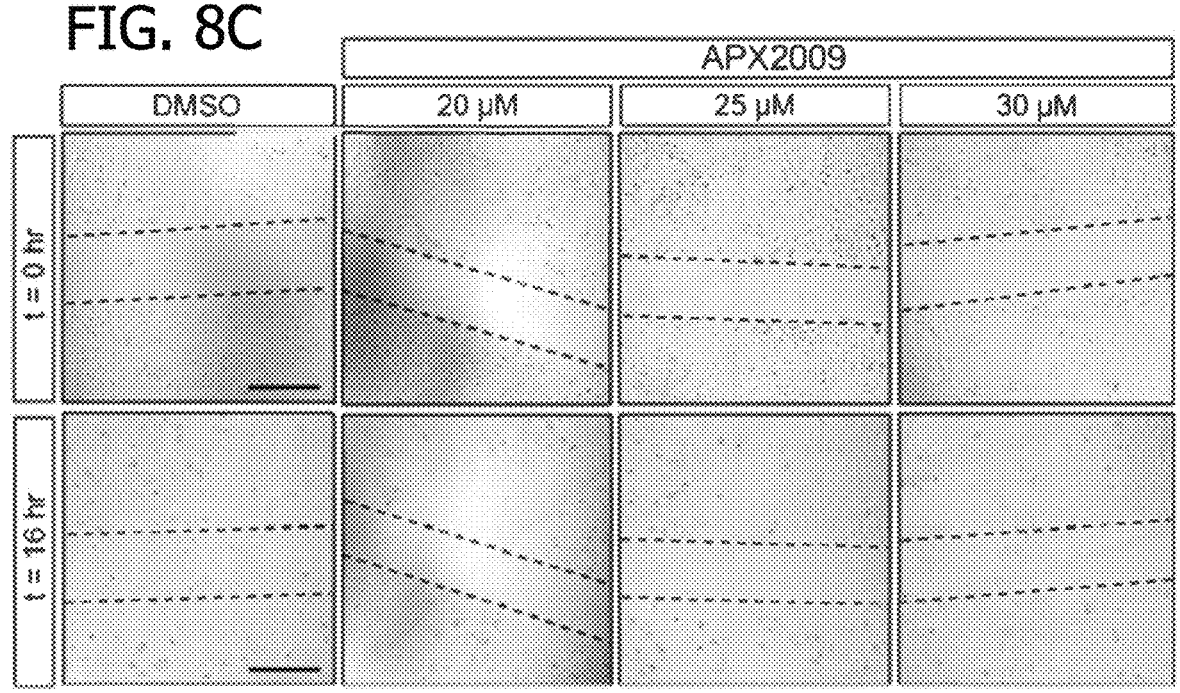
Figure 8D:
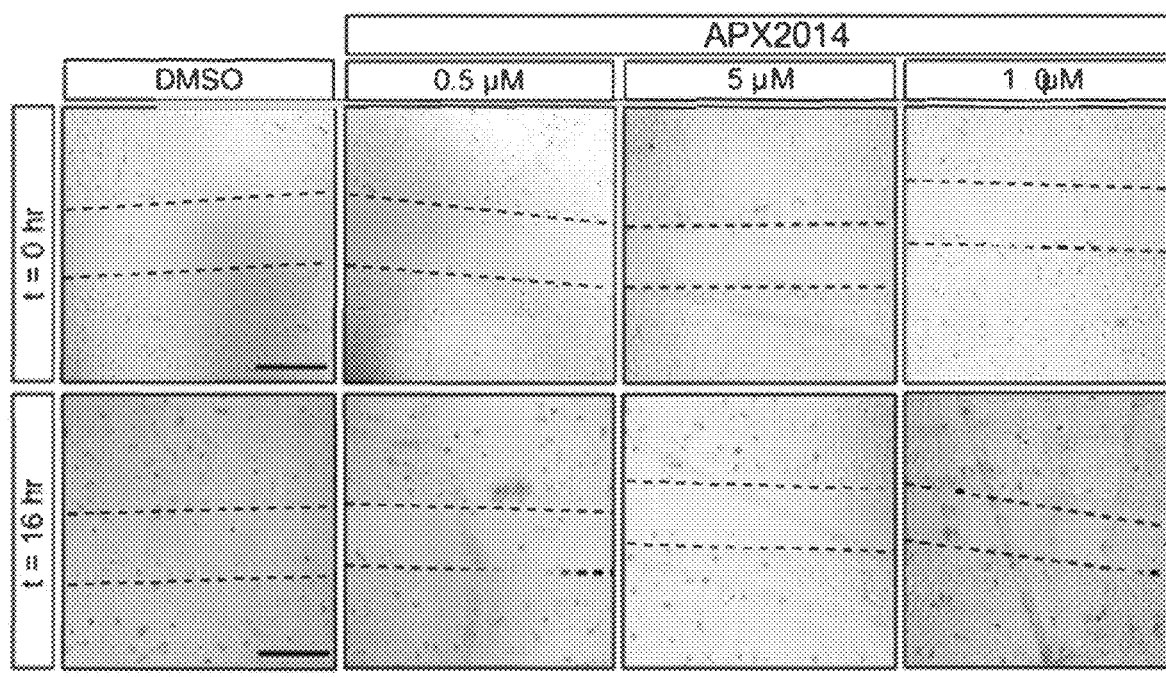
Figure 9A:
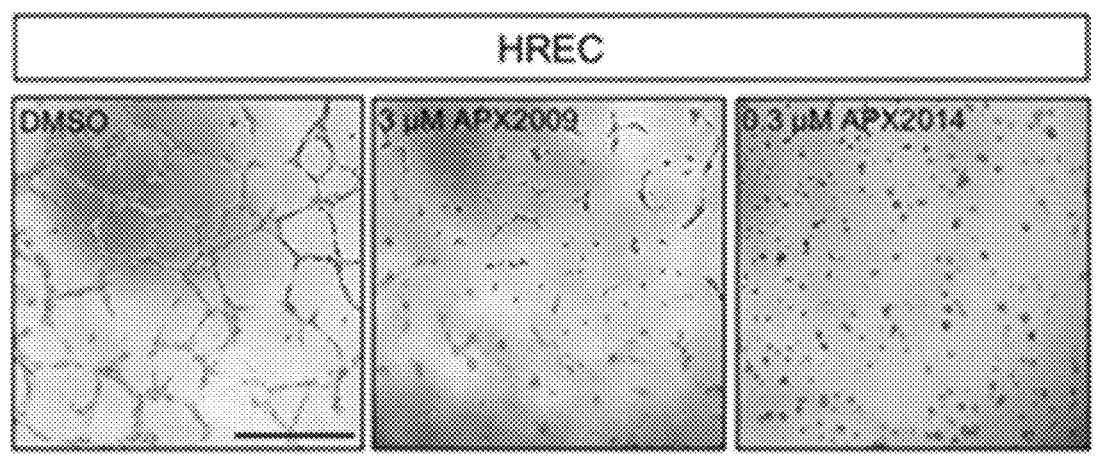
FIGS. 9A-9D depict compounds APX2009 and APX2014 inhibited endothelial tube formation in HRECs and Rf/6a cells in vitro.
Figure 9B:
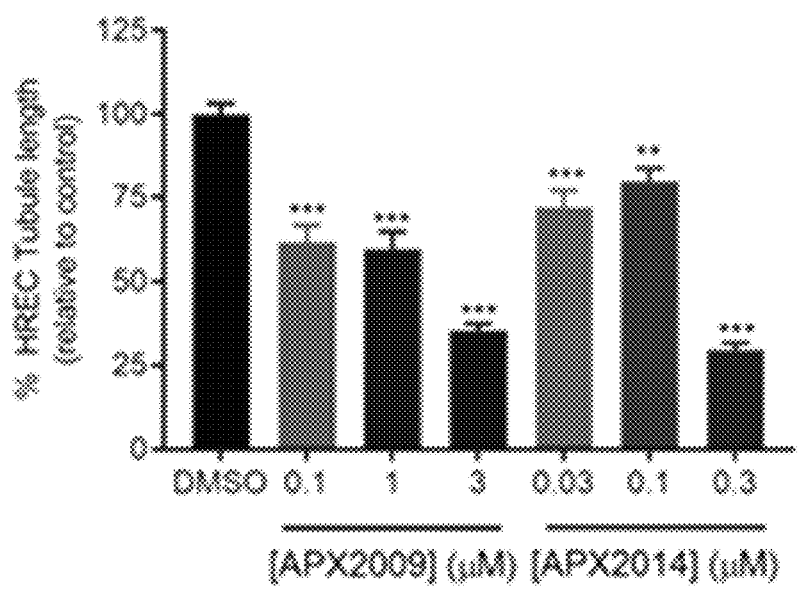
Figure 9C:
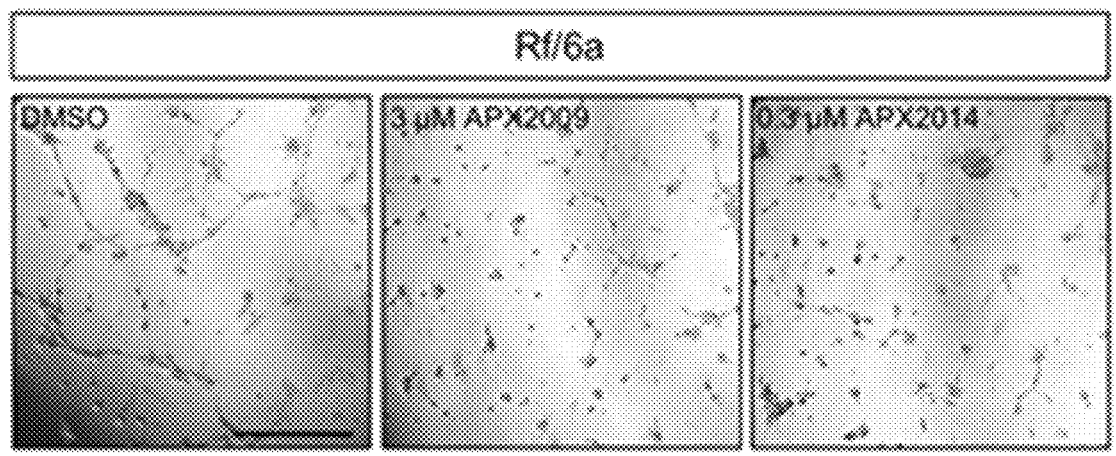
Figure 9D:
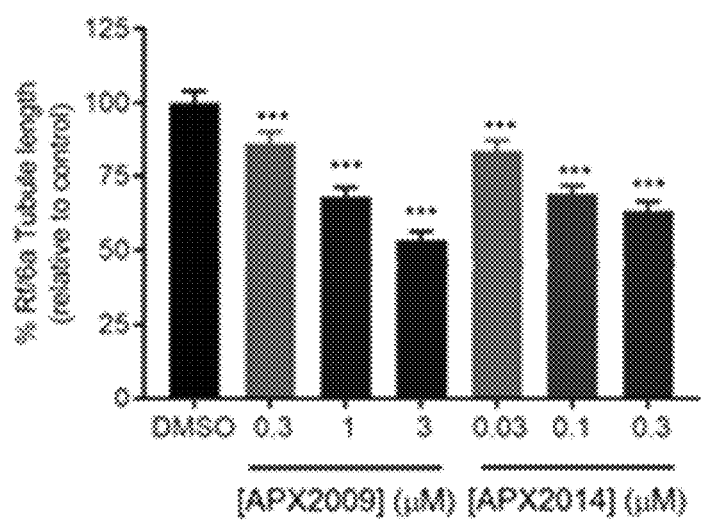
Figure 10A:
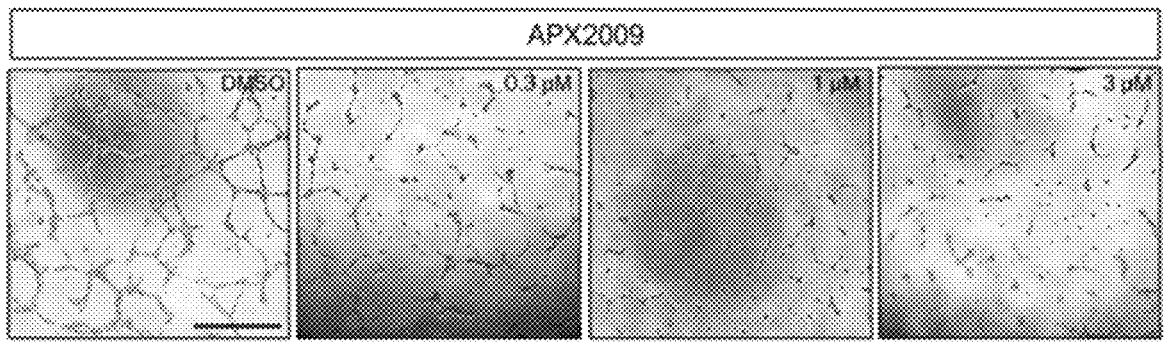
FIGS. 10A-10D depict APX2009 and APX2014 inhibited endothelial tube formation in HRECs in vitro. Tube formation on Matrigel by HRECs in the presence of the indicated concentrations of APX2009 (FIG. 10A) and the indicated concentrations of APX2014 (FIG. 10B) is shown. Further, tube formation on Matrigel by Rf/6a cells in the presence of the indicated concentrations of APX2009 (FIG. 10C) and in the presence of the indicated concentrations of APX2014 (FIG. 10D) is shown. Scale bars=500 µm.
Figure 10B:
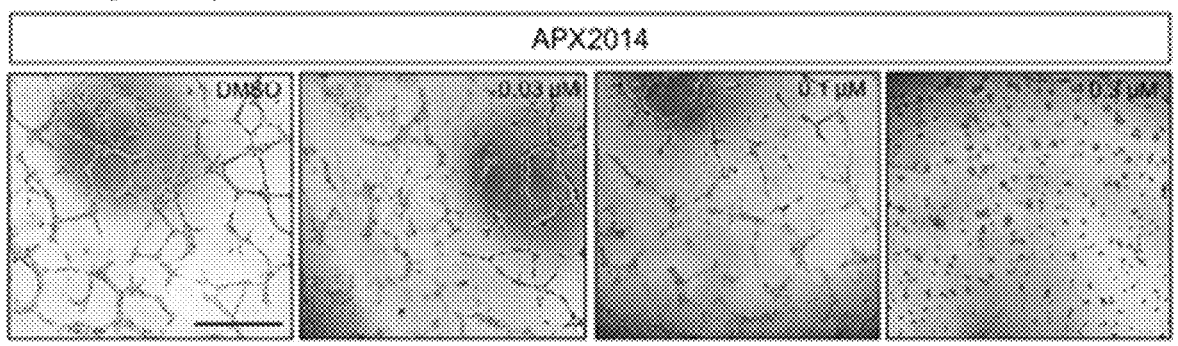
Figure 10C:
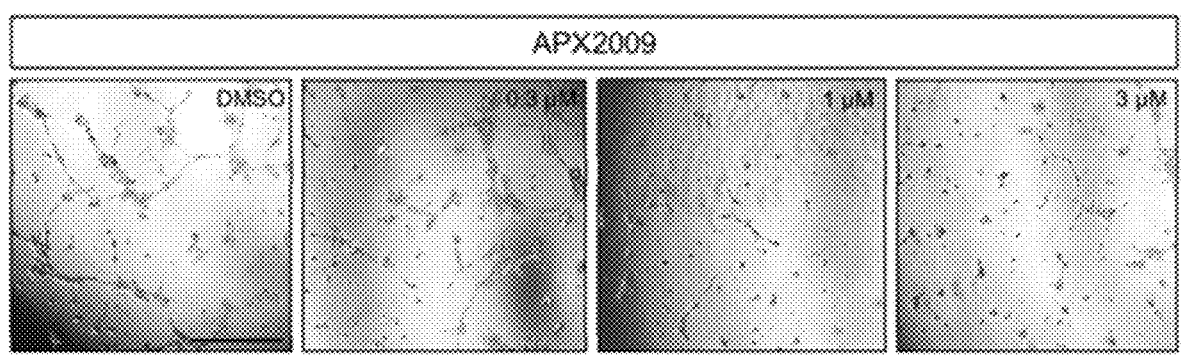
Figure 10D:
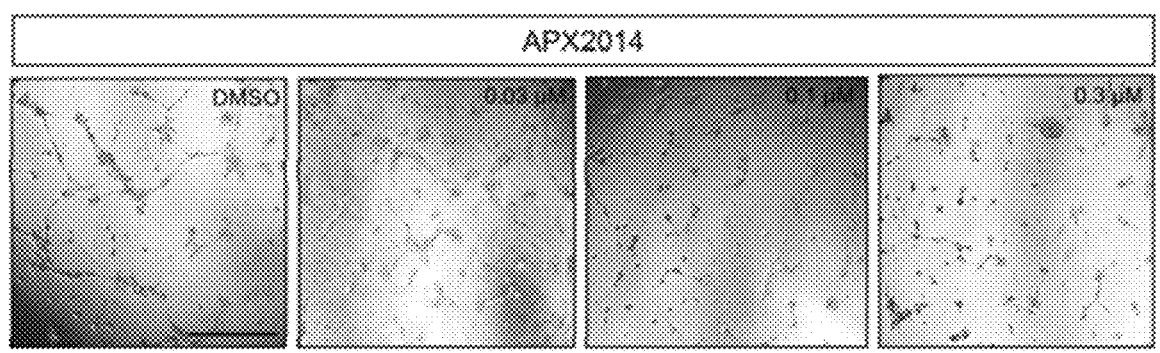

APX2009 and APX2014 blocked S phase without inducing apoptosis. The activity of the compounds were assessed in more detail in HRECs. Both compounds reduced the number of cells going through S phase as evidenced by reduced Ki-67 staining and reduced EdU incorporation (FIGS. 3A-3D; FIGS. 4A & 5). This was also evident as a modest increase in cells in G0/G1 phase at high doses of compound, with a concomitant decrease in G2/M phase cells (FIGS. 4B & 4C). However, neither compound induced apoptosis at anti-proliferative doses as assessed by TUNEL (FIGS. 6A & 6B).

APX2009 and APX2014 blocked endothelial cell migration. Neovascularization involves an array of coordinated events, including extracellular matrix degradation, cell migration, cell proliferation, and morphogenesis of endothelial cells. To know the effect of APX2009 and APX2014 compounds on endothelial cell migration, a scratch-wound assay was performed. (FIGS. 7A-7D; FIGS. 8A-8D). Both compounds again were dose-dependently effective here, without causing obvious cytotoxicity over the short time course of these assays.

APX2009 and APX2014 blocked endothelial cell tube formation. Endothelial cells organize and form capillary-like structures upon plating on an extracellular matrix such as Matrigel. The organization of endothelial cells into a three-dimensional network of tubes is essential for angiogenesis. As such, the Matrigel tube formation assay is a good in vitro predictor of angiogenic potential in vivo. In this assay, both APX2009 and APX2014 inhibited tubule formation markedly, at concentrations lower than those required for inhibiting migration alone, strongly indicative of antiangiogenic activity (FIGS. 9A-9D; FIGS. 10A-10D).

Figure 11A:
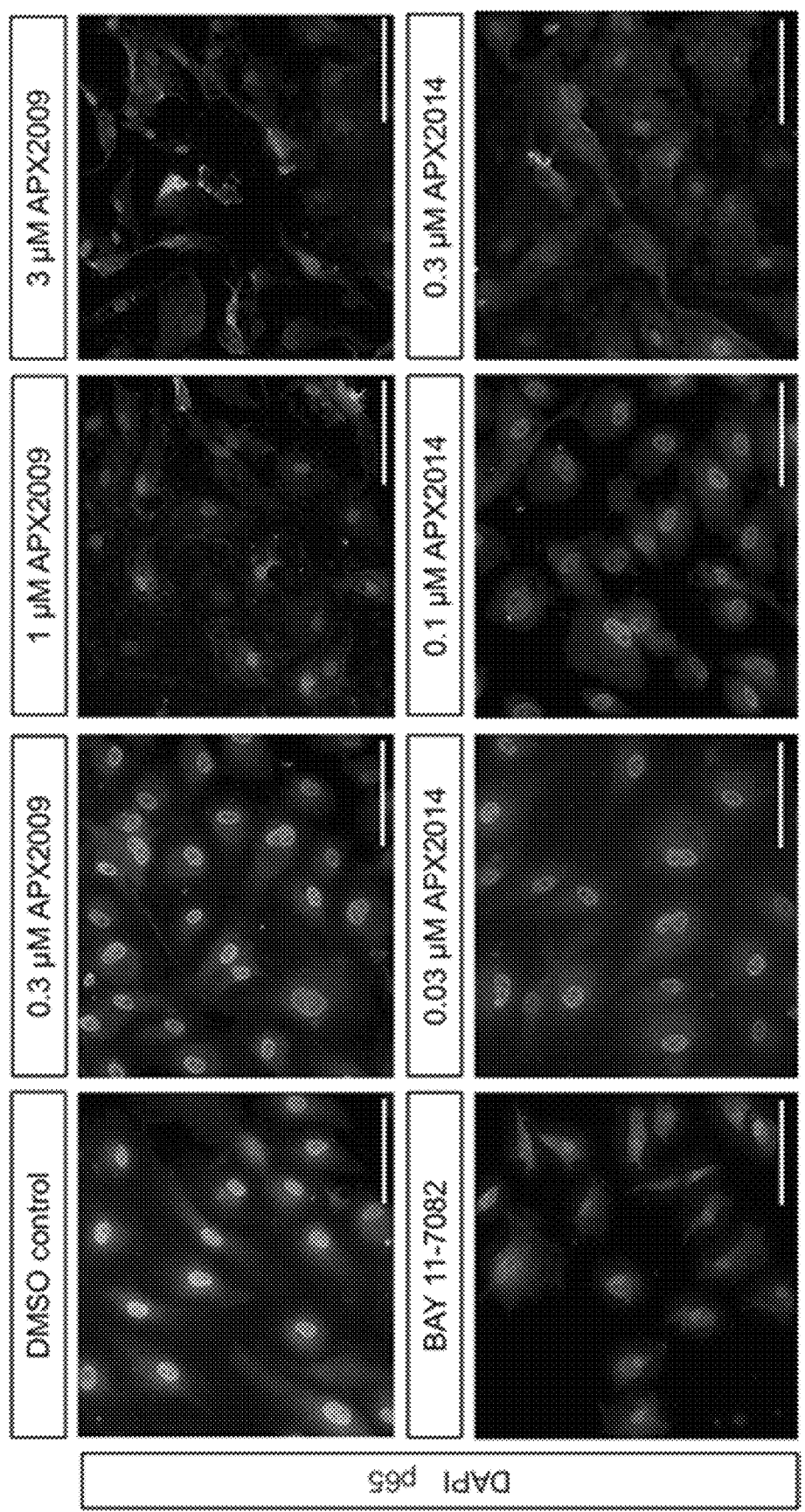
FIGS. 11A-11D depict compounds APX2009 and APX2014 inhibit TNF-α mediated NF-κB signaling and proangiogenic target gene mRNA expression. After treating HRECs with the indicated concentrations of APX2009 and APX2014, p65 (red) was detected by immunofluorescence and nuclei (blue) stained with DAPI; compounds dose-dependently reduced p65 nuclear translocation as evidenced by decreased overlap between red and blue signals. BAY 11-7082 is a positive control NF-κB inhibitor. Scale bar=100 µm.
Figure 11B:
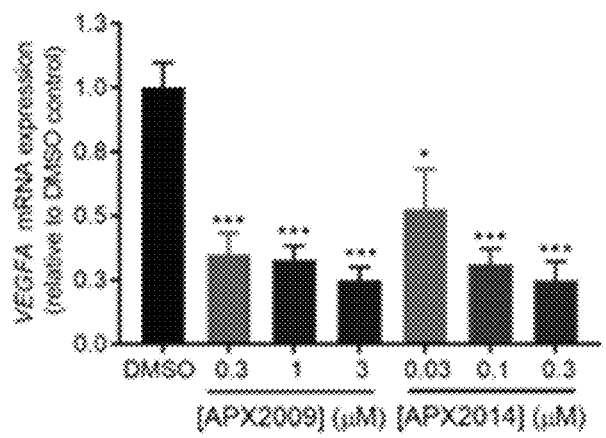
Figure 11C:
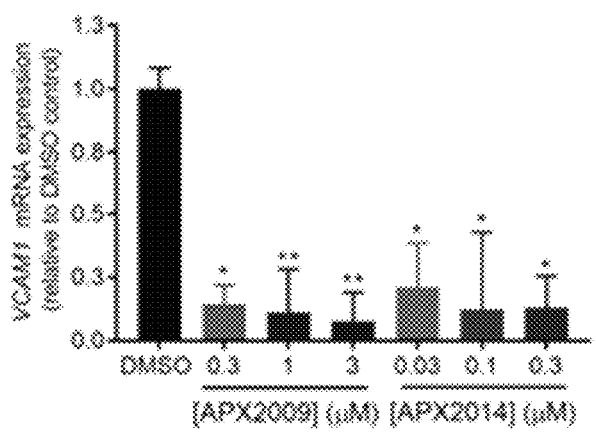
Figure 11D:
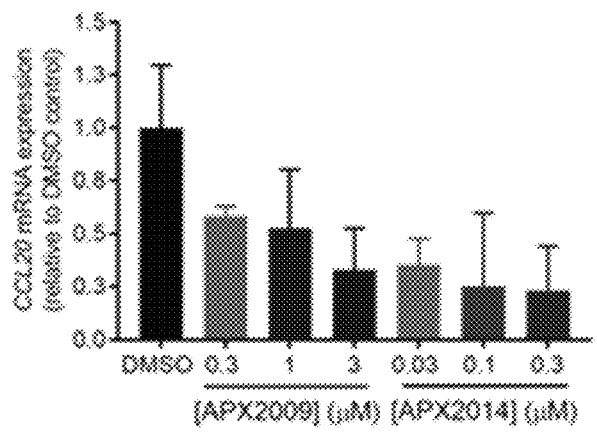

APX2009 and APX2014 inhibited NF-κB activity. Since Ref-1 inhibition has previously been associated with reduction in NF-κB activity (Shah et al., 2017), the activity of this pathway was assessed in response to the compounds in HRECs, to determine if APX2009 and APX2014 were acting through the expected mechanisms. First, the translocation of the p65 subunit of NF-κB into the nucleus was assessed in response to TNF-α, a key indication of pathway activity. Translocation of p65 was dose-dependently attenuated in APX2009 and APX2014-treated HRECs (FIG. 11A). Moreover, production of the mRNA of VEGFA, VCAM1, and CCL20, all of which are downstream of NF-κB, was decreased 3- to 10-fold by these compounds (FIGS. 11B, 11C & 11D).

Figure 12A:
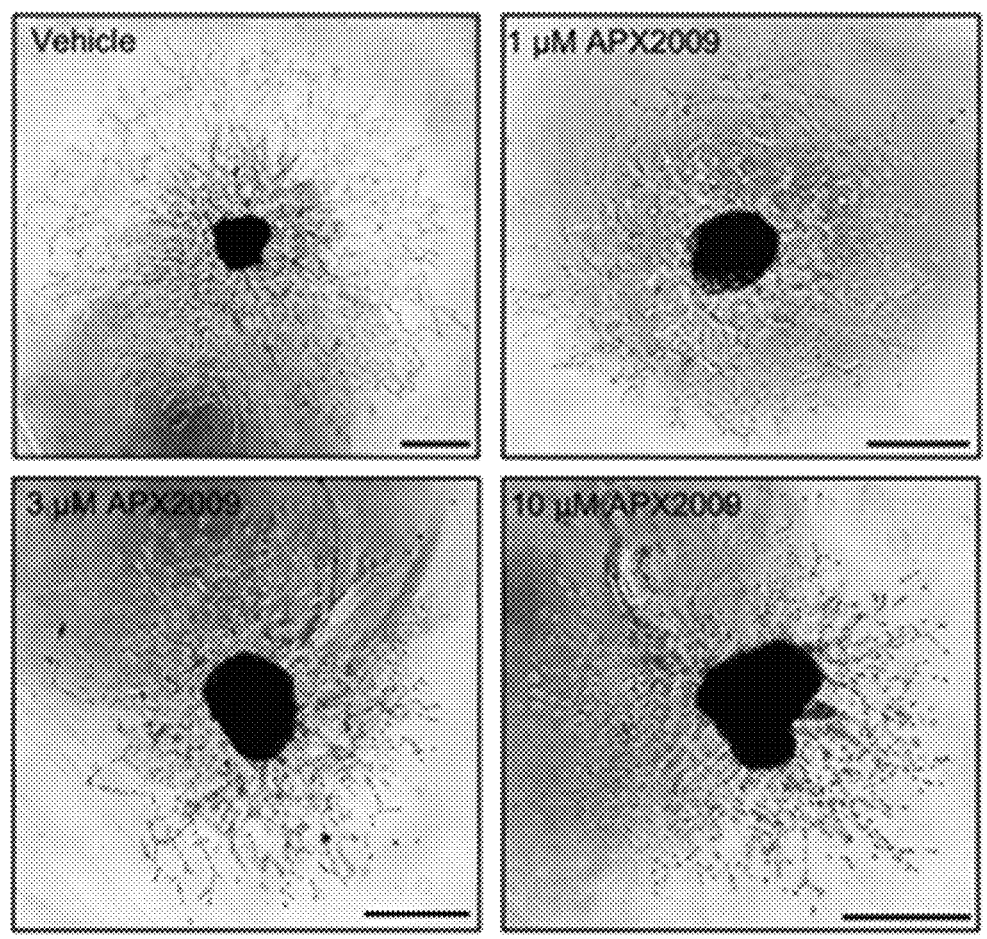
FIGS. 12A-12D depict compounds APX2009 and APX2014 inhibited choroidal sprouting in a concentration-dependent manner
Figure 12B:
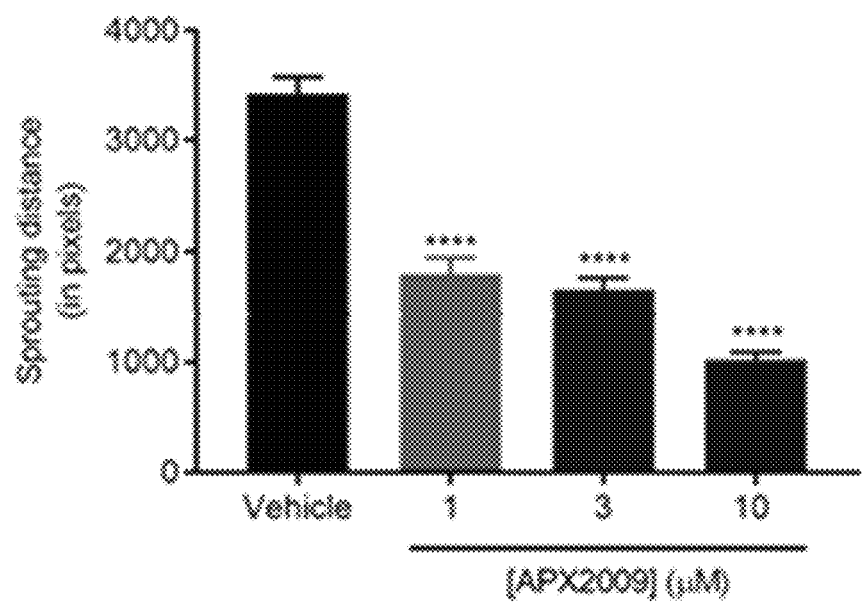
Figure 12C:
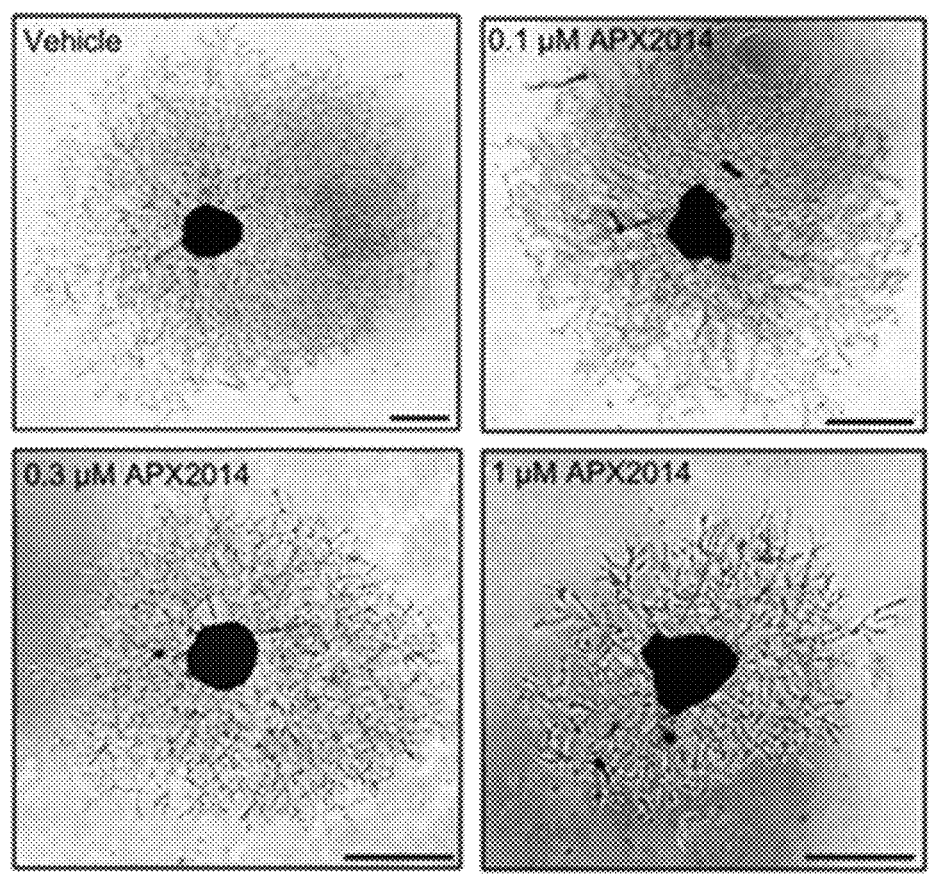
Figure 12D:
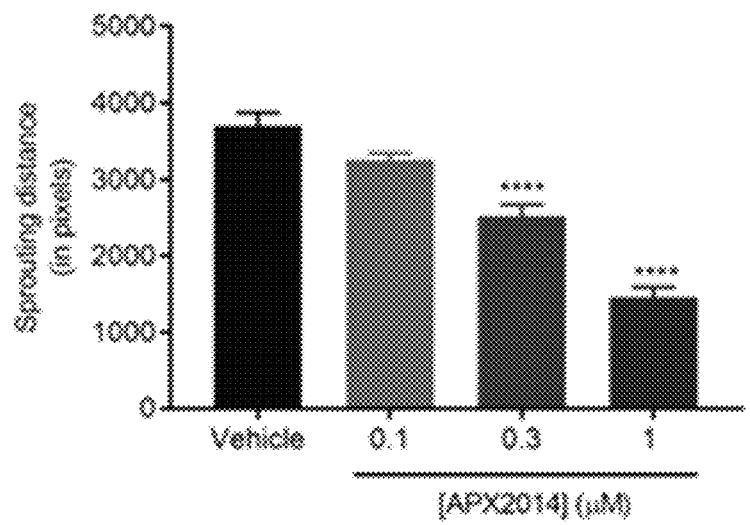

APX2009 and APX2014 blocked angiogenesis ex vivo. As a further test of activity, a choroidal sprouting assay using murine choroidal explants was used to test the efficacy of the APX compounds in a complex microvascular bed in tissues (FIGS. 12A-12D). In this assay, choroidal cells grow out of the choroidal tissue piece into a surrounding Matrigel matrix. Both compounds significantly reduced sprouting, with APX2014 remaining more potent. At 10 µM, APX2009 reduced sprouting by ~70% compared to control (FIGS. 12A & 12B), while at 1 µM (the highest concentration tested), APX2014 reduced sprouting by ~60% compared to control (FIGS. 12C & 12D).

Figure 13A:
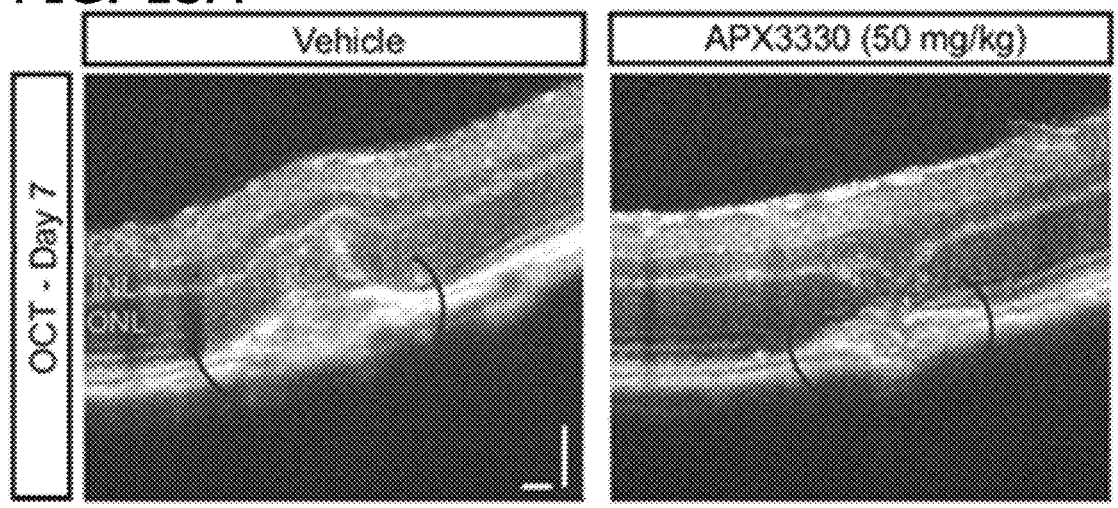
FIGS. 13A-13C depict systemic Ref-1 inhibition with APX3330 blocked neovascularization in the laser-induced choroidal neovascularization (L-CNV) mouse model.
Figure 13B:
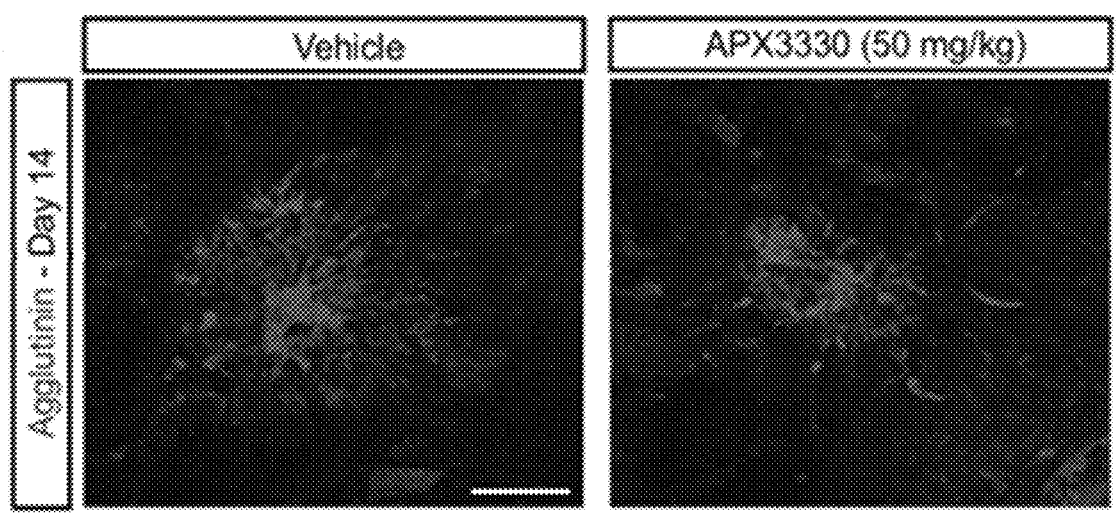
Figure 13C:
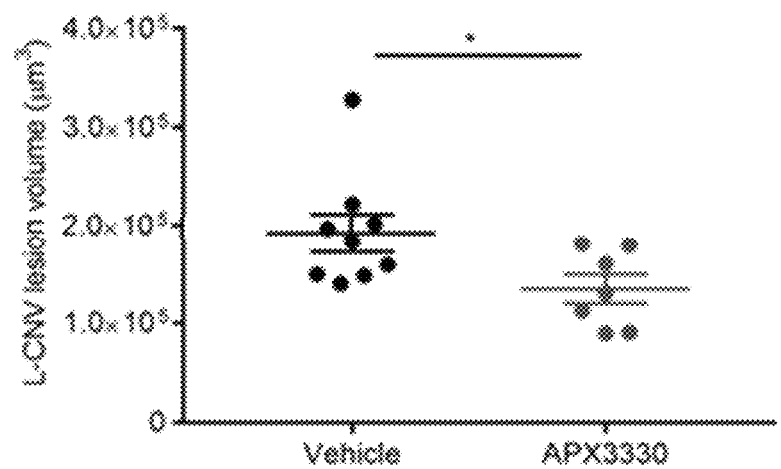

Systemic Ref-1 inhibition with parent compound APX3330 can prevent L-CNV. Previous efforts to attenuate ocular neovascularization by Ref-1 inhibition using APX3330 relied on intravitreal delivery of compound. Although this is the delivery route of the standard-of-care anti-VEGF biologics and ensures that the drug gets to the right place in humans, it is labor-intensive, causes patient discomfort, and incurs a risk of potentially vision-threatening endophthalmitis Thus, it was explored if systemic (intraperitoneal) Ref-1 inhibition could offer an alternative route to therapy of L-CNV. As a proof-of-concept, i.p. injections of the first-generation Ref-1 inhibitor APX3330 (7) delivered 50 mg/kg twice daily, 5 days on/two days off, for two weeks was employed. This dosing regimen was chosen as it was previously successful and non-toxic for preclinical tumor studies. Animals treated with APX3330 displayed significantly reduced L-CNV volume (FIGS. 13A-13C).

Systemic administration of more potent derivative APX2009 reduced L-CNV significantly. Given that APX3330 was an effective systemic agent for L-CNV, the effects of the new second-generation Ref-1 inhibitors were analyzed.

Figures 14A, 14B, 14C:
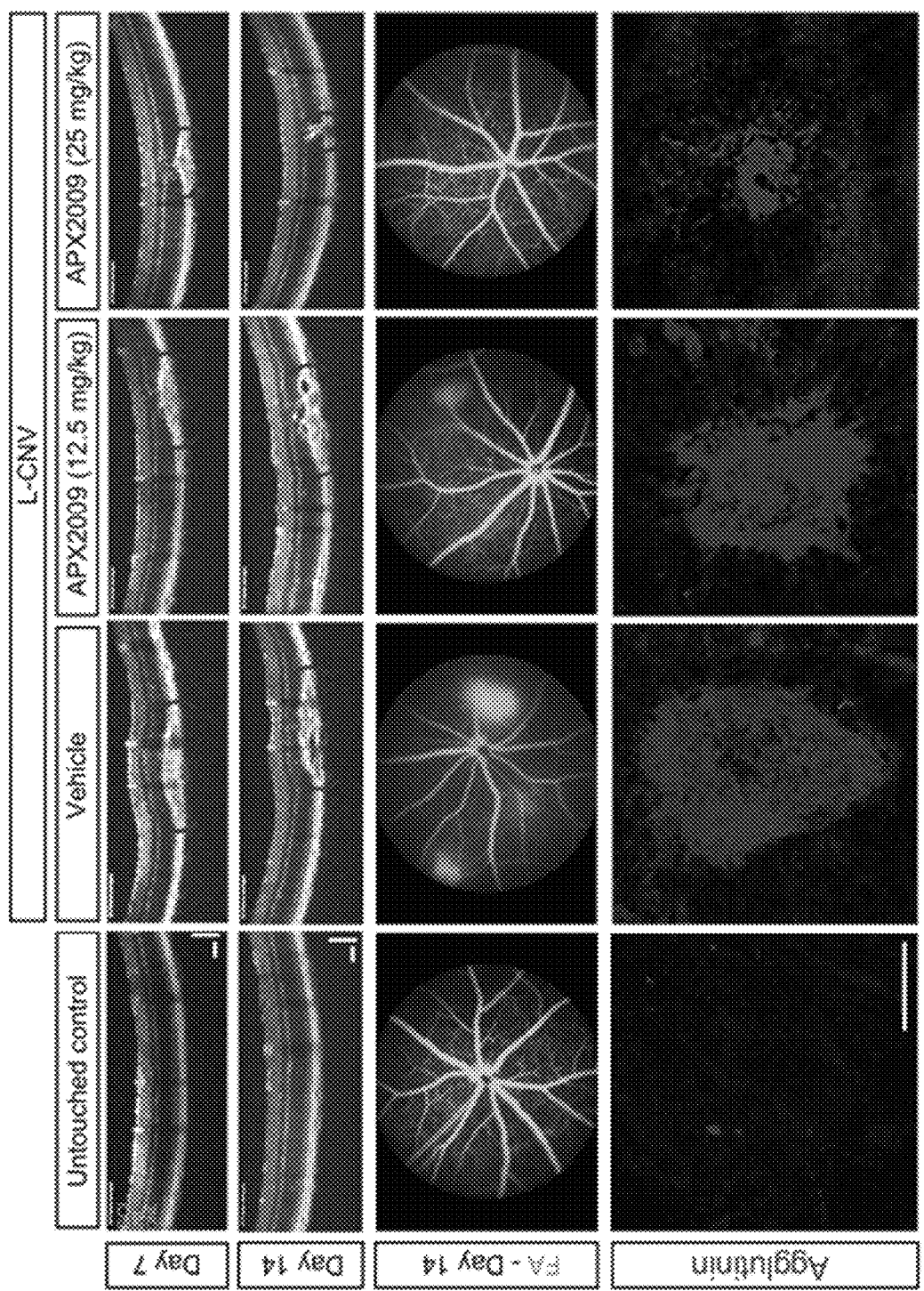
FIGS. 14A-14D depict intraperitoneal APX2009 inhibited choroidal neovascularization in the L-CNV mouse model.
Figure 14D:
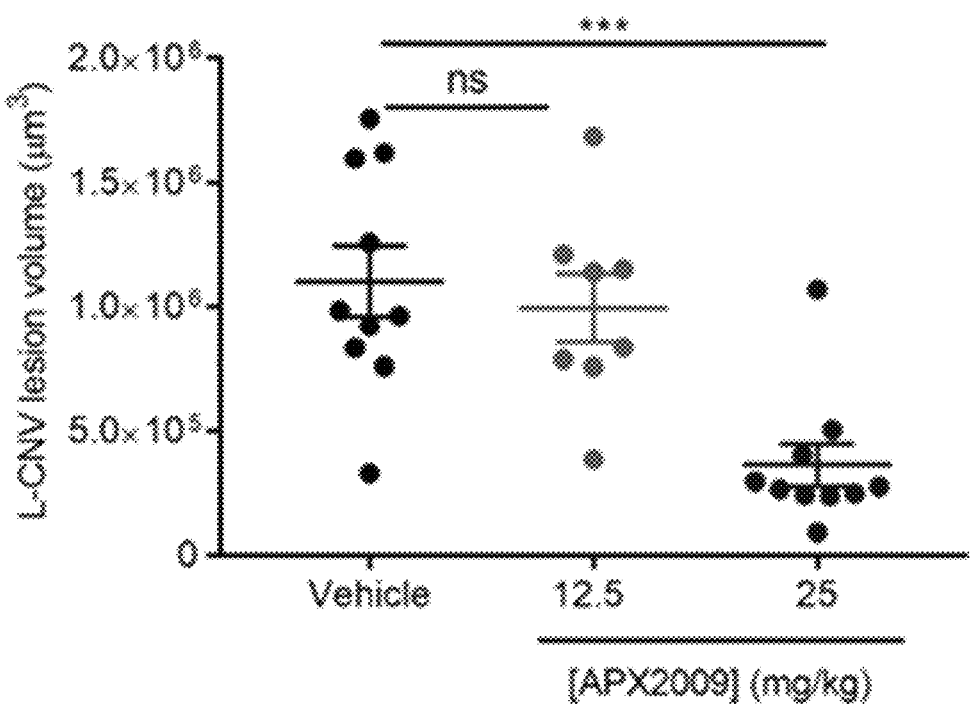
Figure 15A:
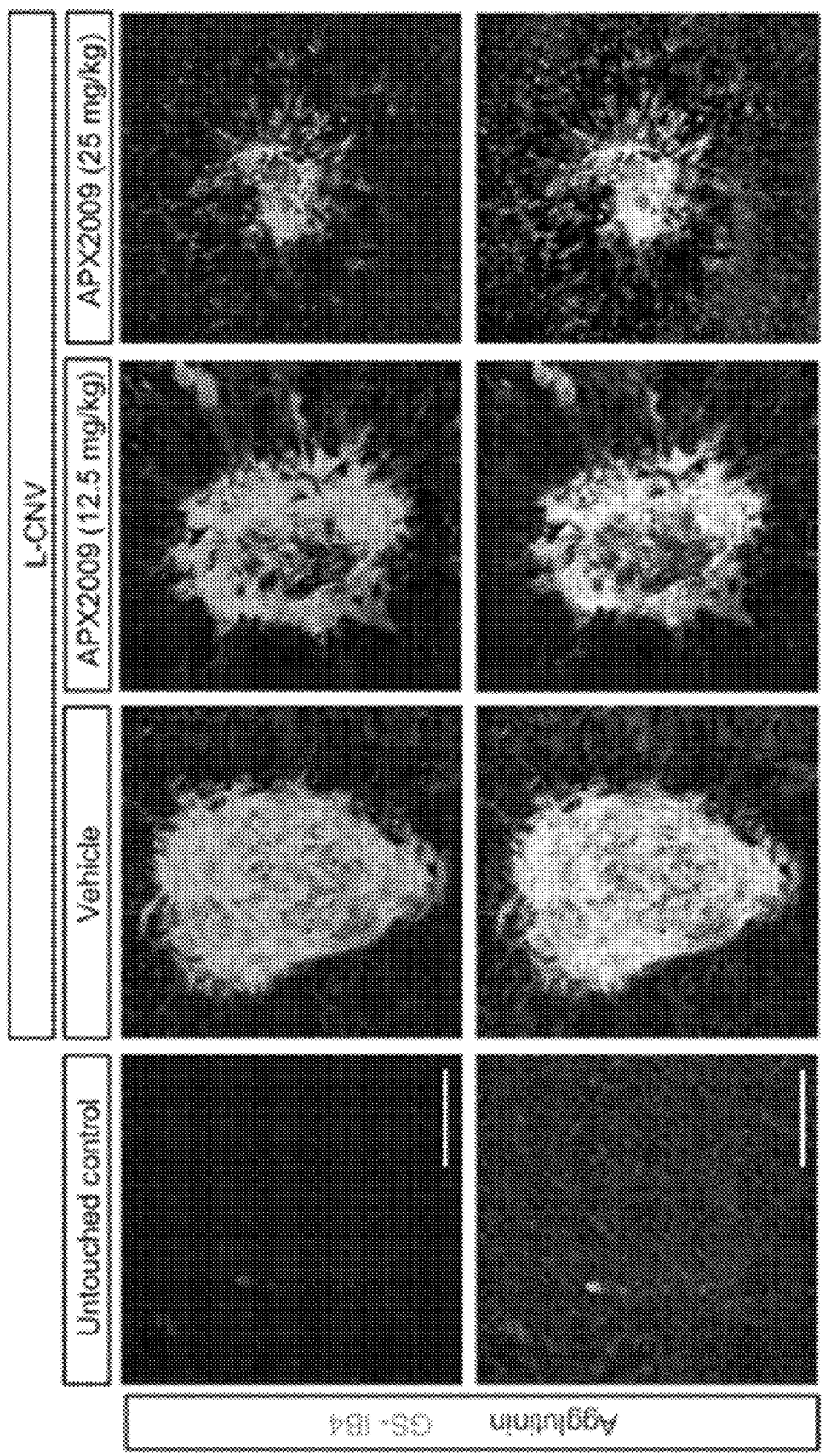
FIGS. 15A-15C depict APX2009 inhibited choroidal neovascularization in the L-CNV mouse model.
Figure 15B:
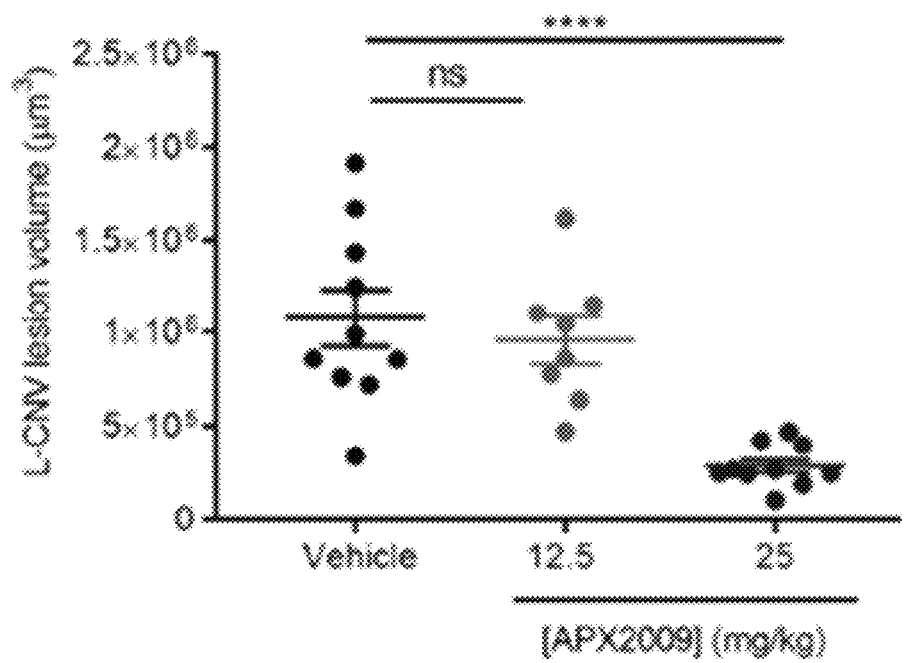
Figure 15C:
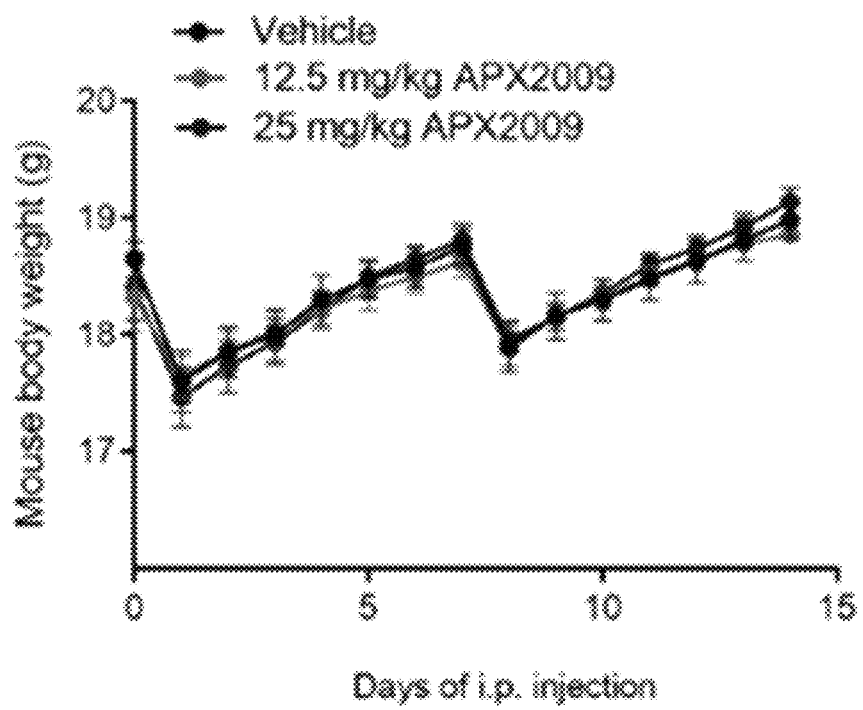

APX2009 was chosen for this experiment as it had previously been safely dosed in animals. Two dosage regimens previously employed, 12.5 or 25 mg/kg, twice daily for two weeks were used. The lower dose did not reduce L-CNV, but the 25 mg/kg dose had a marked effect (FIGS. 14A-14D). This was qualitatively evident by OCT imaging on Day 7, and even more substantial on Day 14 (FIG. 14A). In addition, qualitatively less fluorescein leakage was seen in lesions by fluorescein angiography at Day 14 (FIG. 14B) Finally, L-CNV lesion volume assessed by ex vivo staining with agglutinin (FIG. 14C) and isolectin B4 (FIGS. 15A-15C), was reduced by 25 mg/kg APX2009 approximately four-fold compared to vehicle (FIG. 14D).

The observed effects are likely attributable to redox signaling inhibition, rather than DNA repair inhibition, as the compounds are specific for redox signaling inhibition. The molecularly distinct functional portions of Ref-1, redox and DNA repair, are completely independent. For example, mutations of the cysteine at position 65 (C65A) of APE1/Ref-1 abrogate the redox function, but do not affect DNA repair function, and vice versa. Moreover, Ref-1 inhibitors such as APX3330 do not inhibit APE1 activity. In fact, APX3330 and APX2009 can enhance APE1 repair activity in neurons, potentially contributing to a neuroprotective effect of these agents, which could offer an added benefit in the context of photoreceptor cell death in neovascular eye diseases.

Given their anti-Ref-1 redox signaling activity, APX2009 and APX2014 likely exert their antiangiogenic effects by blocking the activation of transcription factors induced by Ref-1. Likely candidates include NF-κB and HIF-1α, both of which can regulate VEGF. In retinal pigment epithelial cells, APX3330 reduced both NF-κB and HIF-1α activity, with a concomitant reduction in VEGF expression. Additionally, APX3330 treatment of stroke in type one diabetes mellitus rats significantly decreased total vessel density and VEGF expression. The exact transcription factors modulated by Ref-1 inhibition in the context of ocular neovascularization remain to be determined, however.

There was not observed obvious intraocular or systemic toxicity of the two compounds tested in vivo (APX3330 and APX2009), nor was substantial cell death seen in migration, tube formation, and choroidal sprouting assays. These findings are consistent with the excellent safety profile for APX3330 in humans Nonetheless, ocular toxicity of the new compounds and intraocular pharmacokinetics remain to be thoroughly examined.

A well-tolerated, systemic drug therapy has significant potential for treatment of neovascular eye diseases. The existing approved drugs are all biologics requiring intravitreal injection in the context of an ophthalmologist's clinic. An orally bioavailable drug (as with APX3330) could be administered at home, potentially as a once daily pill. The tradeoff for such a therapy would be much more frequent dosing than that required for intravitreal injections (monthly or less), and more substantial systemic exposure than that seen with intravitreal therapies. But given the strong safety profile of Ref-1 inhibitors, this might be manageable. Moreover, patient and healthcare system costs might be significantly lower with such a therapy, as office visits and injection procedures could be reduced.

In summary, it has now been shown for the first time that systemic administration of Ref-1 inhibitors (APX2009 and APX2014) can attenuate L-CNV. As L-CNV is a widely-used model of the choroidal neovascularization that underlies wet AMD, suggesting that Ref-1 inhibition could find therapeutic utility for this indication. The in vitro data suggest that Ref-1 inhibition also effectively blocks angiogenesis involving retinal endothelial cells. Thus, these inhibitors may also be useful for retinal neovascular diseases like ROP and PDR.

Example 2

In this Example, the effects of Ref-1 knockdown on NF-κB signaling-associated genes was analyzed.

Human retinal endothelial cells (HRECs) (Cell Systems, Inc. Kirkland, Wash.) were plated in 6-well plates and treated with 0.1 µM APX2009, 1 µM APX2009 or DMSO for 6 hours and 24 hours. Cells were washed once after treatment with PBS, collected and frozen. This process was repeated to collect treated cells in 4 different passages. RNA was extracted in 300 µL Trizol (Life Technologies, Carlsbad, Calif.) and flash frozen at −80° C. The SMARTer system (Clontech, Mountain View, Calif.) was used to generate cDNA from cells. The dscDNA quantity and quality was assessed using an Agilent Bioanalyzer (Agilent Technologies, Santa Clara, Calif., USA) with the High Sensitivity DNA Chip. A total of 48 SCR and 48 siAPE1 cells were chosen for sequencing. The IUSM Genomics Facility prepared libraries using a Nextera kit (Illumina, San Diego, Calif.). DNAs were sequenced using the Illumina HiSeq 4000.

Figure 16:
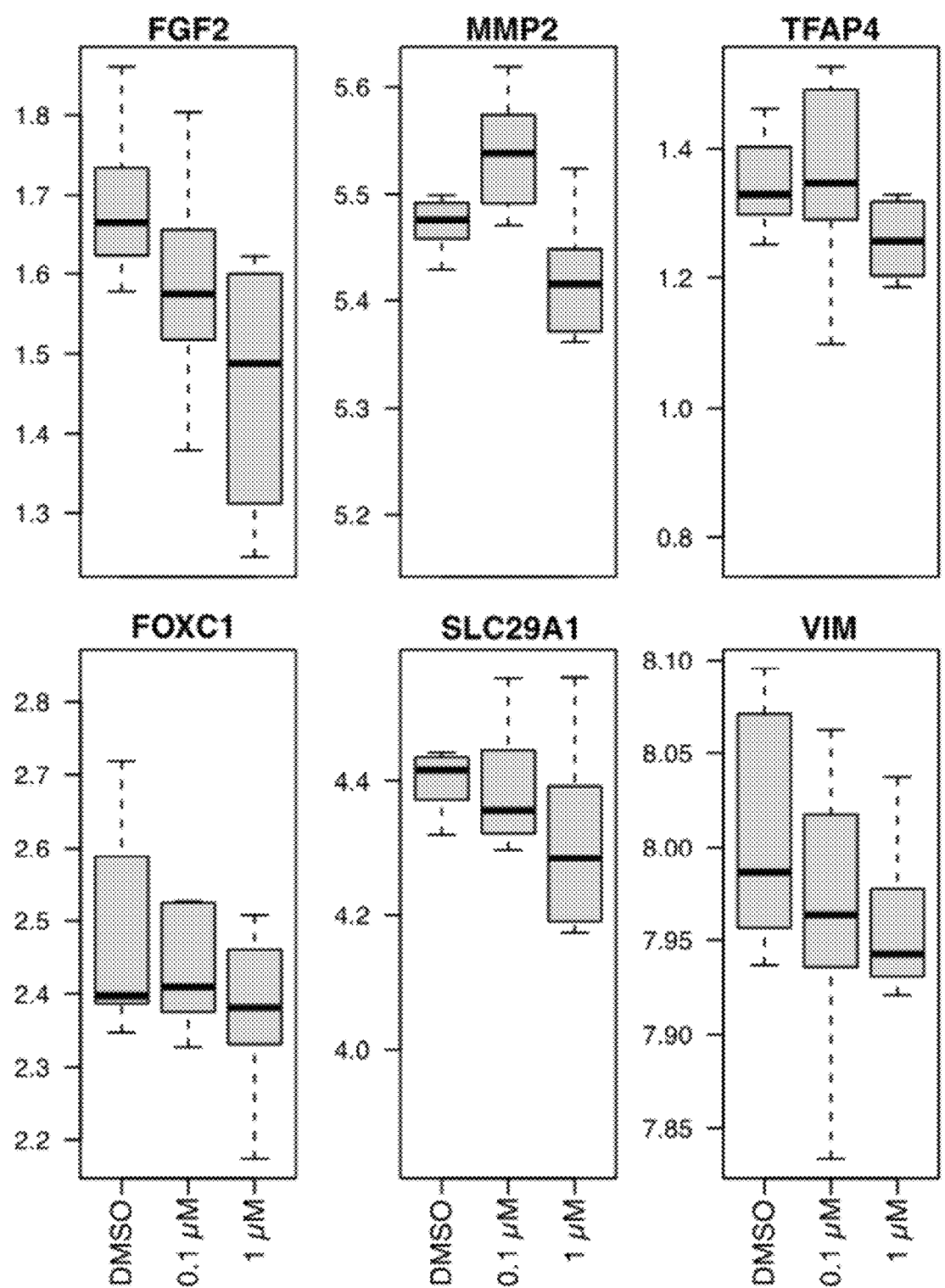
FIG. 16 depicts sample data of known HIF-regulated genes that are downregulated by indicated concentrations of APX2009 in HRECs. RNA-Seq data were analyzed by principal component (PC) regression, with significant genes having r>0.42 with respect to association with the PC of APX2009 treatment. Pathway enrichment analysis revealed enrichment of these genes regulated by HIF1A (p=0.02).

Ref-1 activates NF-κB and HIF-1α signaling: Redox-dependent stabilization of the HIF-1α protein is required for activation of HIF-1, and redox signaling through Ref-1 regulates the DNA-binding activity of HIF-1. Hypoxia-driven gene expression is not solely through HIF; other TFs that respond to hypoxia include NF-κB, AP-1, and others. Molecular changes induced by hypoxia can impact upon angiogenesis, both in the eye and in cancer. Novel compounds APX2009 and APX2014 inhibit NF-κB activation and reduce target gene expression in HRECs. This was confirmed in this RNA-Seq experiment demonstrating that APX2009 blocked HIF regulated genes in a concentration dependent manner (FIG. 16).

Example 3

In this Example, the role of Ref-1 on ocular angiogenesis is analyzed.

The Protein Atlas was mined for expression data on Ref-1. In addition, immunohistochemistry was performed for Ref-1 in de-identified postmortem eye tissue from a wet AMD patient and an age-matched control. Tissue sections were deparaffinized. DAB was used for detection and counterstained with DAPI. Images of retina and choroid were taken on an EVOS fl digital microscope.

Figure 17:
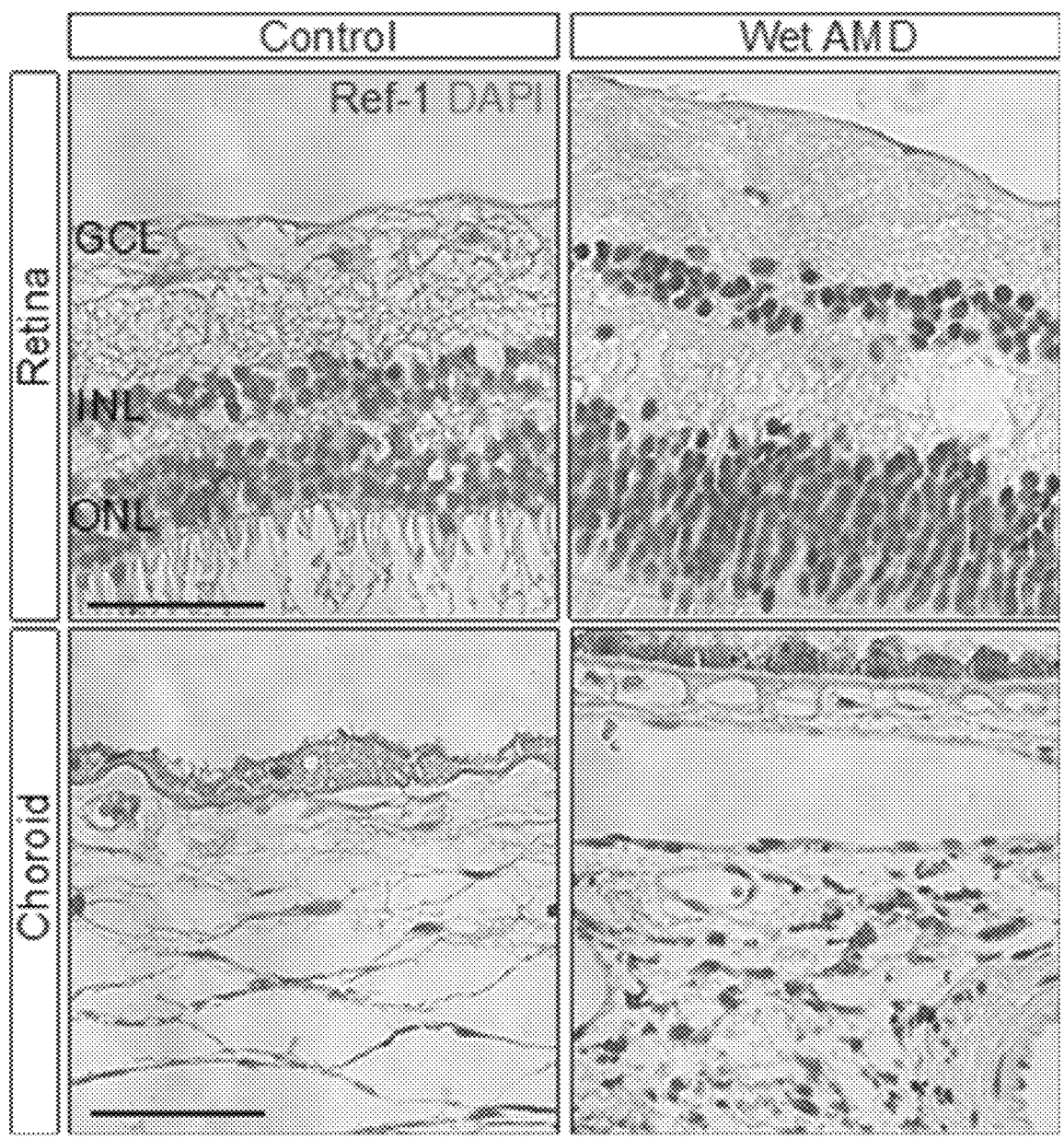
FIG. 17 depicts Ref-1 being upregulated in wet AMD. Sections of human eye stained for Ref-1 (brown) revealed expression in nuclei of the inner nuclear layer (INL), outer nuclear layer (ONL), and choroid, specifically in wet AMD, but not age-matched control. Scale bar=50 µm. GCL, ganglion cell layer.

Ref-1 is highly expressed in developing murine retinas, as well as retinal pigment epithelium (RPE) cells, retinal pericytes, choroidal endothelial cells (CECs) and retinal endothelial cells (RECs). At the RNA level, it is expressed higher in retina than in all but a third of 36 other tissue types (https://www.proteinatlas.org/ENSG00000100823-APEX1/tissue). Preliminary evidence also suggests that it is upregulated in the retina and choroid of human wet AMD patient eyes compared with age-matched controls (FIG. 17), suggesting disease relevance.

What is claimed is:

1. A method of inhibiting ocular neovascularization in a subject in need thereof, the method comprising administering to the subject an effective amount of an apurinic/apyrimidinic endonuclease 1 redox factor 1 inhibitor selected from the group consisting of [(2E)-2-[(3-methoxy-1,4-dioxo-1,4-dihydronaphthalen-2-yl)methylidene]-N,N-diethylpentanamide], (2E)-2-[(3-methoxy-1,4-dioxo-1,4-dihydronapthalen-2-yl)methylidene]-N-methoxypentanamide], pharmaceutically acceptable salts or pharmaceutically acceptable solvates thereof.

2. The method as set forth in claim 1, wherein the apurinic/apyrimidinic endonuclease 1 redox factor 1 inhibitor is [(2E)-2-[(3-methoxy-1,4-dioxo-1,4-dihydronaphthalen-2-yl)methylidene] -N,N-diethylpentanamide] and the subject is administered from about 12.5 mg/kg to about 35 mg/kg [(2E)-2-[(3-methoxy-1,4-dioxo-1,4-dihydronaphthalen-2-yl)methylidene] -N,N-diethylpentanamide] per day.

3. The method as set forth in claim 1, wherein the apurinic/apyrimidinic endonuclease 1 redox factor 1 inhibitor is (2E)-2-[(3-methoxy-1,4-dioxo-1,4-dihydronapthalen-2-yl)methylidene] -N-methoxypentanamide] and the subject is administered from about 12.5 mg/kg to about 35 mg/kg (2E)-2-[(3-methoxy-1,4-dioxo-1,4-dihydronapthalen-2-yl)methylidene] -N-methoxypentanamide] per day.

4. The method as set forth in claim 1 further comprising administering at least one additional therapeutic agent to the subject selected from the group consisting of an anti-VEGF treatment, vitamins, minerals and combinations thereof.

5. The method as set forth in claim 1, wherein the subject has a disease selected from the group consisting of proliferative diabetic retinopathy (PDR), diabetic retinopathy, wet age-related macular degeneration (AMD), pathological myopia, hypertensive retinopathy, occlusive vasculitis, polypoidal choroidal vasculopathy, diabetic macular edema, uveitic macular edema, central retinal vein occlusion, branch retinal vein occlusion, corneal neovascularization, retinal neovascularization, ocular histoplasmosis, neovascular glaucoma, retinoblastoma, and combinations thereof.

6. A method of treating wet age-related macular degeneration in a subject in need thereof, the method comprising administering to the subject an effective amount of an apurinic/apyrimidinic endonuclease 1 redox factor 1 inhibitor selected from the group consisting of [(2E)-2-[(3-methoxy-1,4-dioxo-1,4-dihydronaphthalen-2-yl)methylidene] -N,N-diethylpentanamide], (2E)-2-[(3 -methoxy- 1,4-dioxo-1,4-dihydronapthalen-2-yl)methylidene]-N-methoxypentanamide], pharmaceutically acceptable salts or pharmaceutically acceptable solvates thereof.

7. The method as set forth in claim 6, wherein the apurinic/apyrimidinic endonuclease 1 redox factor 1 inhibitor is [(2E)-2-[(3-methoxy-1,4-dioxo-1,4-dihydronaphthalen-2-yl)methylidene] -N,N-diethylpentanamide] and the subject is administered from about 12.5 mg/kg to about 35 mg/kg [(2E)-2-[(3-methoxy-1,4-dioxo-1,4-dihydronaphthalen-2-yl)methylidene] -N,N-diethylpentanamide] per day.

8. The method as set forth in claim 6, wherein the apurinic/apyrimidinic endonuclease 1 redox factor 1 inhibitor is (2E)-2-[(3-methoxy-1,4-dioxo-1,4-dihydronapthalen-2-yl)methylidene] -N-methoxypentanamide] and the subject is administered from about 12.5 mg/kg to about 35 mg/kg (2E)-2-[(3-methoxy-1,4-dioxo-1,4-dihydronapthalen-2-yl)methylidene]-N-methoxypentanamide] per day.

9. The method as set forth in claim 6 further comprising administering at least one additional therapeutic agent to the subject selected from the group consisting of an anti-VEGF treatment, vitamins, minerals and combinations thereof.

* * * * *